(12) United States Patent
Leying et al.

(10) Patent No.: US 9,416,398 B2
(45) Date of Patent: *Aug. 16, 2016

(54) GENERIC BUFFER FOR AMPLIFICATION

(75) Inventors: Hermann Leying, Rotkruez (CH); Dirk Zimmermann, Zug (CH)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 522 days.

This patent is subject to a terminal disclaimer.

(21) Appl. No.: 13/224,547

(22) Filed: Sep. 2, 2011

(65) Prior Publication Data

US 2012/0064511 A1 Mar. 15, 2012

(30) Foreign Application Priority Data

Sep. 7, 2010 (EP) .................................... 10175555

(51) Int. Cl.
*C12P 19/34* (2006.01)
*C12Q 1/68* (2006.01)

(52) U.S. Cl.
CPC .................................... *C12Q 1/6806* (2013.01)

(58) Field of Classification Search
CPC ............... C12Q 1/6813; C12Q 1/6876; C12Q 2600/118; G01N 2333/435; G01N 33/53
USPC ....................................................... 435/91.2
See application file for complete search history.

(56) References Cited

U.S. PATENT DOCUMENTS

| 6,942,971 B2 * | 9/2005 | McMillan et al. ......... 435/287.2 |
|---|---|---|
| 2010/0041040 A1 | 2/2010 | Babiel et al. |

FOREIGN PATENT DOCUMENTS

| EP | 11179688 | 11/2011 |
|---|---|---|
| EP | 11179688.4 | 1/2013 |
| WO | WO 0043534 | * 7/2000 |

OTHER PUBLICATIONS

Edwards et al (multiple PCR, Advantages, Development and applications, in PCR methods and Applications), Cold Spring Harbor Lab Press, 1994.*
Wittwer et al., (Real-Time Multiplex PCR Assays, Methods, 25; 430-442, 2001.*
COBAS (R) AmpliPrep / COBAS (R) TagMan (R) HIV-1 Test, XP007915387.
"cobas s 201 Donor Screening. World-class pooling." XP007915386., 2009.
"cobas s 201 system for NAT Donor Screening. One Vision. Many Possibilities." XP007915385., 2007.
R. Holeva, et al., 2006, "Real-time PCR detection and quantification of vector trichodorid nematodes and Tobacco rattle virus", Molecular and Cellular Probes, 20:203-211.
Quan, Phenix-Lan, et al., 2008, "Rapid sequence-based diagnosis of viral infection", Antiviral Research, 79:1-5.
Smith, C., "Adventures with Multiplex Real-Time PCR", biocompare, the Buyer's Guide for Life Scientists., pp. 1-2, 2010.
Watzinger, F., et al., 2004, "Real-Time Quantitative PCR Assays for Detection and Monitoring of Pathogenic Human Viruses in Immunosuppressed Pediatric Patients", Journal of Clinical Microbiology, 42(11):5189-5198. , 2004.
Meng, Q., et al., 2001, "Automated Multiplex Assay System for Simultaneous Detection of Hepatitis B Virus DNA, Hepatitis C Virus RNA, and Human Immunodeficiency Virus Type 1 RNA", Journal of Clinical Microbiology, 39 (8):2937-2945.
Roche Molecular Systems, 2009, "cobas TM TagScreen MPX Test for use on the cobas s 201 system".
Lai, Guan-Hua, et al., 2005, "erbB-2/neu Transmformed Rat Cholangiocytes Recapitulate Key Cellular and Molecular Features of Human Bile Duct Cancer", Gastroenterology, 129:2047-2057.
Burkhardt, Brant, R., et al., 2005, "Tissue-specific and glucose-responsive expression of the pancreatic derived factor (PANDER) promoter", Biochimica et Biophysica Acta, 1730:215-225.
Zhang, Yuhua, et al.; 2007, "Isolation of an osmotin-like protein gene from strawberry and analysis of the response of this gene to abiotic stresses", Journal of Plant Physiology, 164:67-77.

* cited by examiner

*Primary Examiner* — Cynthia B Wilder
(74) *Attorney, Agent, or Firm* — David J Chang

(57) ABSTRACT

The present invention relates to a method of amplifying a first and a second target nucleic acid in separate reaction receptacles, wherein said reaction receptacles comprise a solution comprising amplification reagents and oligonucleotides specific for said first or said second target nucleic acid, wherein said solution is the same for amplifying said first target nucleic acid and said second target nucleic acid.

9 Claims, 9 Drawing Sheets

Fig. 2
Fig. 2a
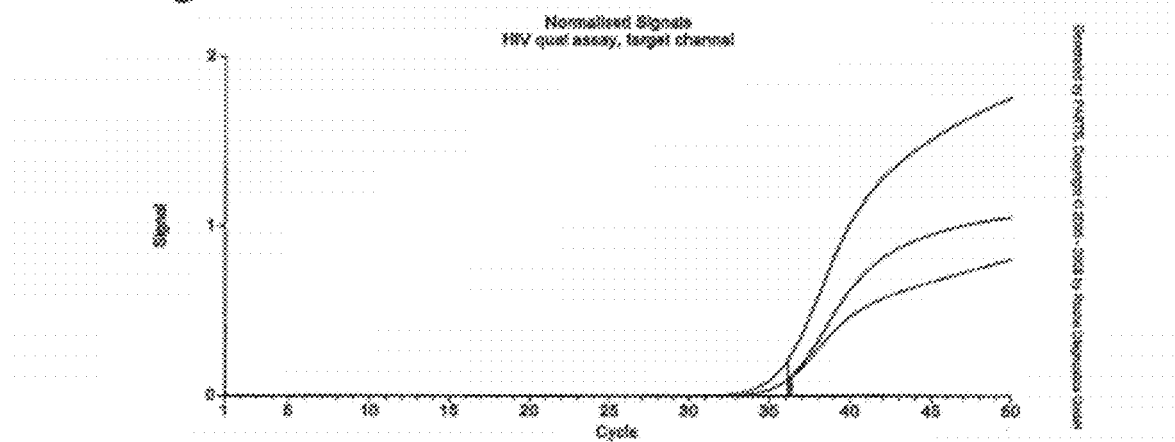
Fig. 2b
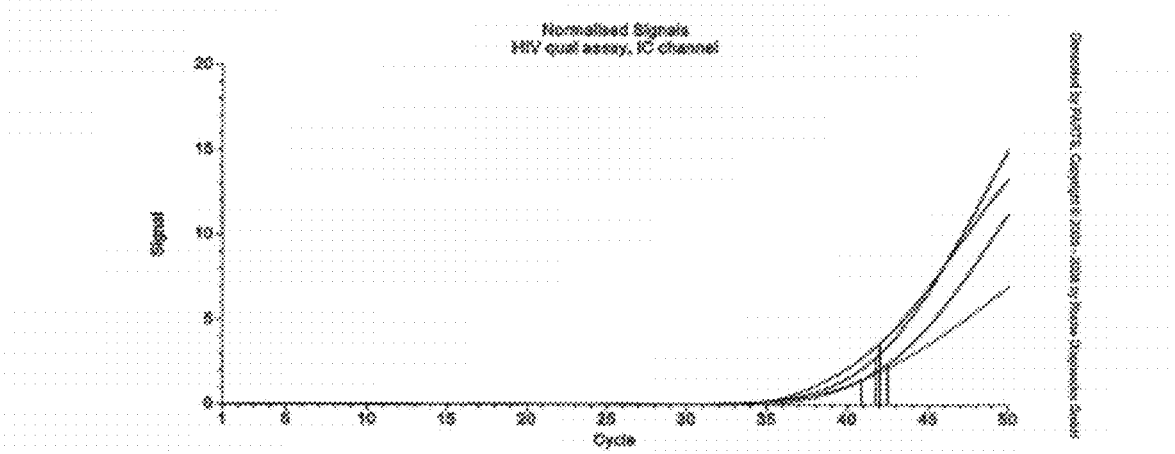

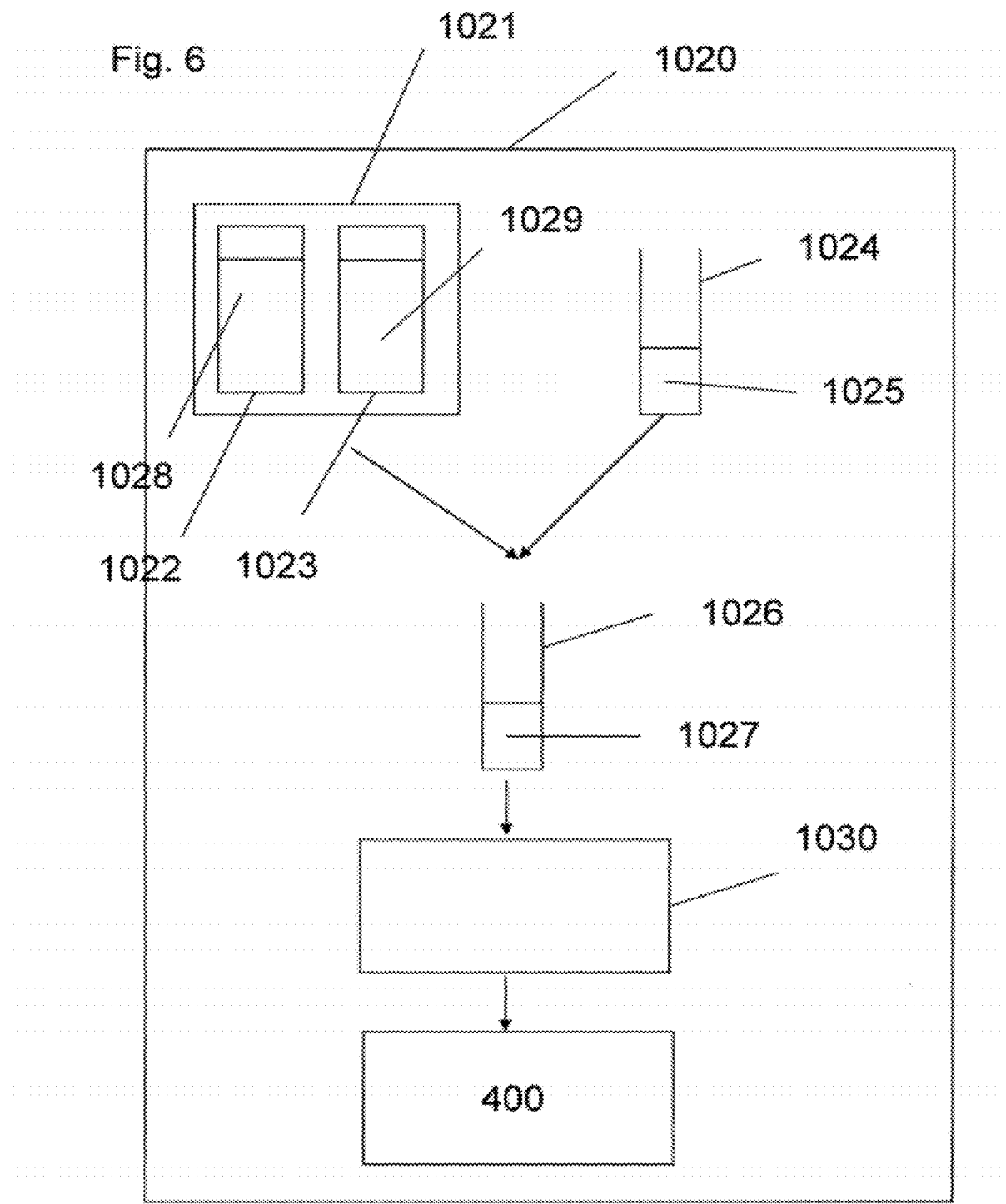

GENERIC BUFFER FOR AMPLIFICATION

REFERENCE TO RELATED APPLICATION

This application claims priority to and benefit of European Patent Application Number EP 10175555.1, filed on Sep. 7, 2010, which is hereby incorporated by reference in its entirely.

REFERENCE TO SEQUENCE LISTING

This application contains a Sequence Listing submitted as an electronic text file named "26769_US_Sequence_Listing", having a size in bytes of 19 kb, and created on Aug. 30, 2011. The information contained in this electronic file is hereby incorporated by reference in its entirety pursuant to 37 CFR §1.52(e)(5).

FIELD OF THE INVENTION

The present invention relates to nucleic acid amplification processes. Such processes are commonly used in research as well as for in-vitro diagnostic testing.

BACKGROUND

In the field of nucleic acid research and molecular diagnostics, the amplification of nucleic acids from numerous sources has been of considerable significance. Examples for diagnostic applications of nucleic acid amplification and detection are the detection of viruses such as Human Papilloma Virus (HPV), West Nile Virus (WNV) or the routine screening of blood donations for the presence of Human Immunodeficiency Virus (HIV), Hepatitis-B (HBV) and/or C Virus (HCV). Furthermore, said amplification techniques are suitable for bacterial targets such as mycobacteria or *Chlamydia trachomatis* and *Neisseria gonorrhoeae*, or the analysis of oncology markers.

The most prominent and widely-used amplification technique is Polymerase Chain Reaction (PCR). Other amplification reactions comprise, among others, the Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification.

Existing commercially available tests, in particular for diagnostics, comprise reagents which are optimized for each test to give good testing efficiency.

The present invention provides improved methods, systems, processes, kits and reagents for testing different types of parameters.

SUMMARY OF THE INVENTION

The present invention relates to a process for amplifying at least a first and a second target nucleic acid that may be present in at least one fluid sample. Said process comprises separately incubating in at least two reaction vessels said nucleic acids with a solution comprising amplification reagents, and oligonucleotides specific for said first or second target nucleic acid, wherein said amplification reagents comprise a polymerase with reverse transcriptase activity, for a period of time and under conditions suitable for transcription of RNA by said polymerase with reverse transcriptase activity to occur. Following this first incubation, the target nucleic acids are incubated separately in the at least two reaction vessels with the solution comprising amplification reagents, and oligonucleotides specific for said first or second target nucleic acid for a period of time and under conditions sufficient for an amplification reaction indicative of the presence or absence of said first and second target nucleic acid to occur.

In the process, the solution in the first and in the second reaction vessels comprises the same proportion of amplification reagents. Oligonucleotides for the first target nucleic acid are present in the first of the at least two reaction vessels and absent in the second of the at least two reaction vessels, and oligonucleotides for the second target nucleic acid are present in the second of the at least two reaction vessels and absent in the first of the at least two reaction vessels.

The present invention also relates to a system for isolating and amplifying at least two different nucleic acids that may be present in at least one sample. The system comprises
  a separation station constructed and arranged to separate said nucleic acids from other material,
  a kit comprising at least one container, said at least one container comprising a solution comprising amplification reagents,
  a first solution comprising oligonucleotides for amplifying a first target nucleic acid,
  a second solution comprising oligonucleotides for amplifying a second target nucleic acid,
  an amplification station comprising reaction vessels,
The solution comprising amplification reagents and the first or the second solution comprising oligonucleotides are combined such that said reaction vessels comprise amplification reagents, separated target nucleic acid and oligonucleotides, wherein the proportion of amplification reagents is identical in reaction vessels comprising oligonucleotides for amplifying the first target nucleic acid, and in reaction vessels comprising oligonucleotides for amplifying the second target nucleic acid.

The invention further relates to a kit for separately reverse transcribing and amplifying at least a first and a second target nucleic acid in separate reaction vessels, said kit comprising at least one container, wherein said container comprises a solution comprising a polymerase with reverse transcriptase activity and lacking oligonucleotides.

Furthermore, the invention relates to a method for separately amplifying at least two different target nucleic acid that may be present in at least one fluid sample. The method comprises providing at least one container comprising a solution for amplifying a target nucleic acid and lacking oligonucleotides. A volume of said solution is transferred to at least two containers, and oligonucleotides specific for amplifying a first target nucleic acid to the first of said containers, and oligonucleotides specific for amplifying a second target nucleic acid to the second of said containers are added. The oligonucleotides may also be transferred to the containers before adding the solution. The contents of the containers are then mixed. Then, the first and second container are loaded into an automated analyzer for automatically amplifying said first and second target nucleic acid. In the analyzer, the first target nucleic acid is combined with a volume of the mixed contents of the first container in a first reaction vessel, and the second target nucleic acid is combined with a volume of the mixed content of the second container in a second reaction vessel. After this step, the contents of the reaction vessels are incubated for a period of time and under conditions sufficient for an amplification reaction indicative of the presence or absence of the first and second target nucleic acid to occur.

The growth curves of HIV and HBV are shown along with the growth curves of the corresponding internal control nucleic acid. The respective target nucleic acid curves are represented by straight lines, the control nucleic acid curves by dotted lines.

FIG. 2a: Qualitative HIV assay, measured in the channel for detection of the target probe.

FIG. 2b: Qualitative HIV assay, measured in the channel for detection of the control probe.

Figure 2C:
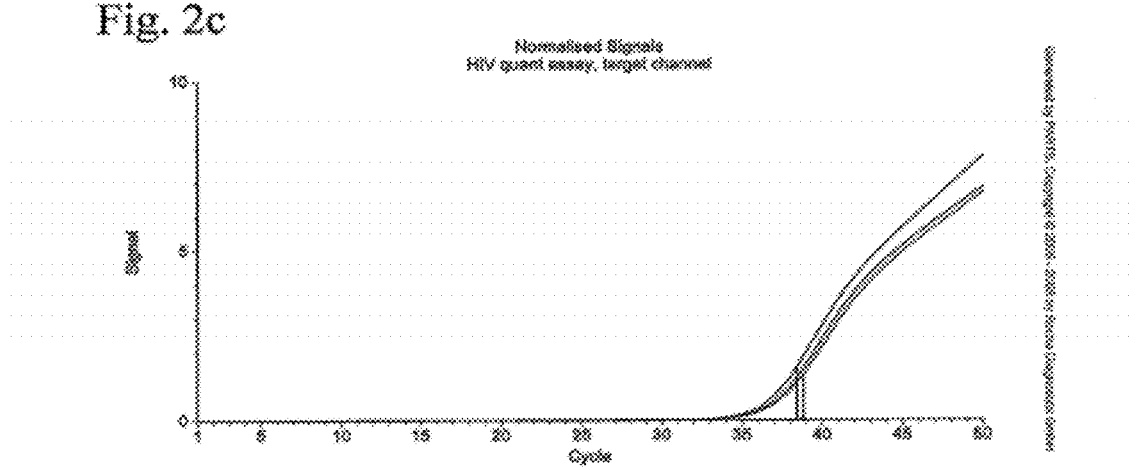
FIG. 2: Growth curves of the amplifications of the target nucleic acids derived from HIV, HBV and CT carried out on a LightCycler480 (Roche Diagnostics GmbH, Mannheim, Del.) as described in Example 1. The "Signal" indicated on the y-axis is a normalized fluorescent signal. The x-axis shows the number of the respective PCR cycle.

FIG. 2c: Quantitative HIV assay, measured in the channel for detection of the target probe.

Figure 2D:
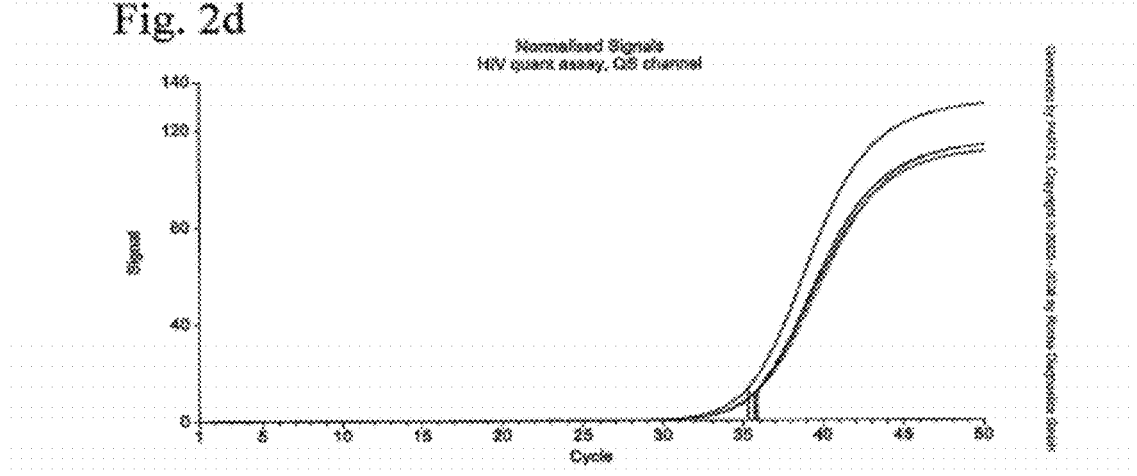

FIG. 2d: Quantitative HIV assay, measured in the channel for detection of the control probe.

Figure 2E:
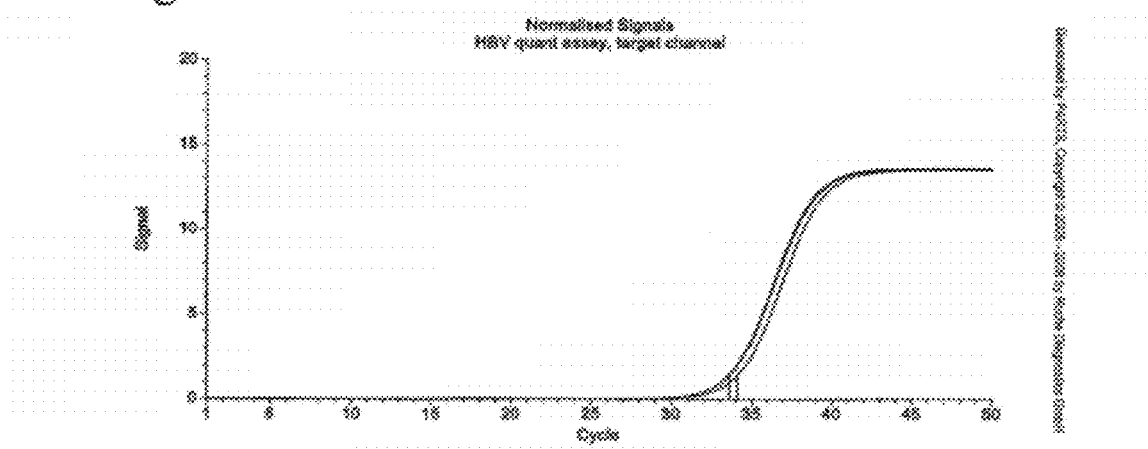

FIG. 2e: Quantitative HBV assay, measured in the channel for detection of the target probe.

Figure 2F:
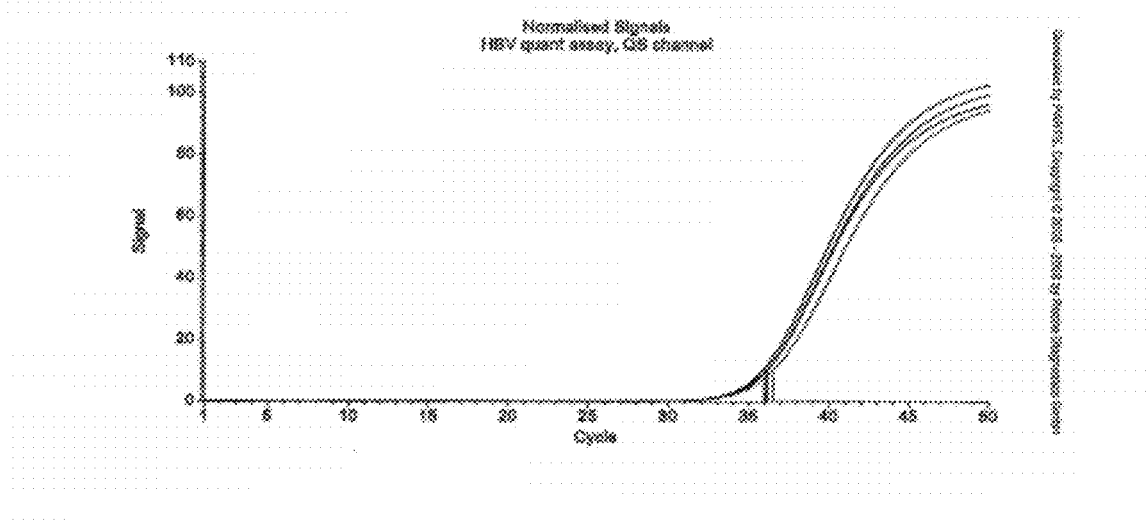

FIG. 2f: Quantitative HBV assay, measured in the channel for detection of the control probe.

Figure 2G:
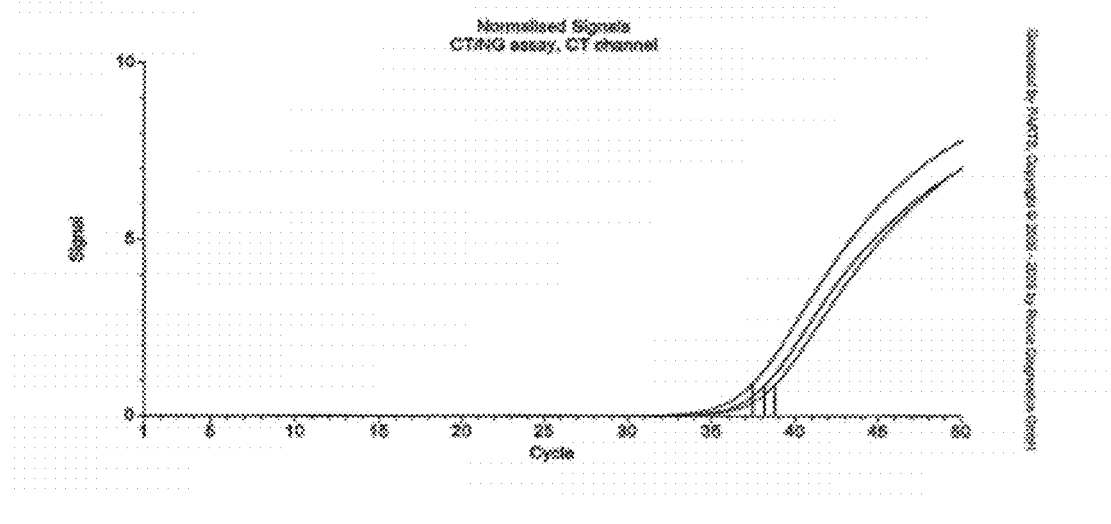

FIG. 2g: CT assay, measured in the channel for detection of the target probe.

Figure 3:
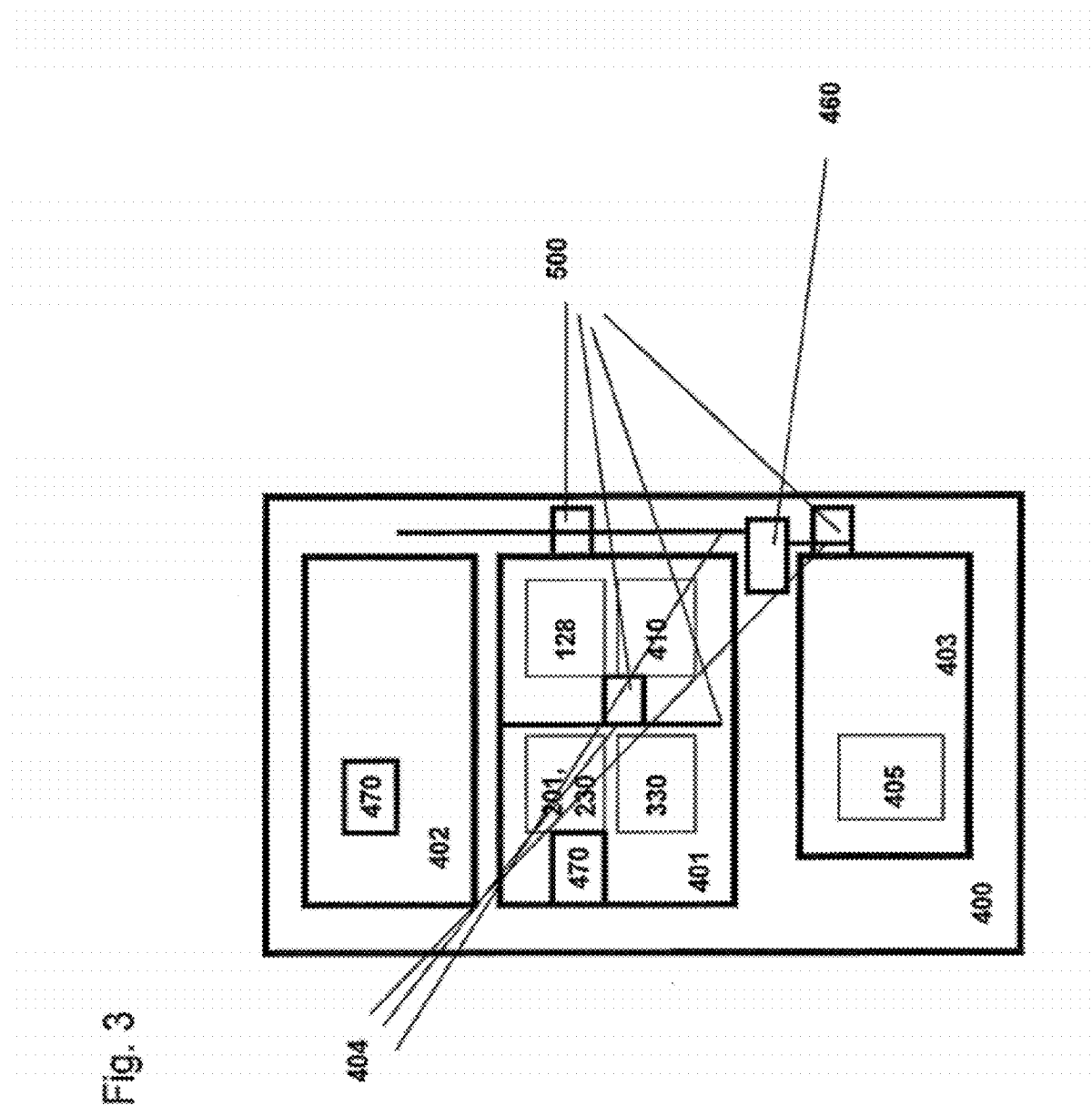

FIG. 3: Analytical system

Figure 4:
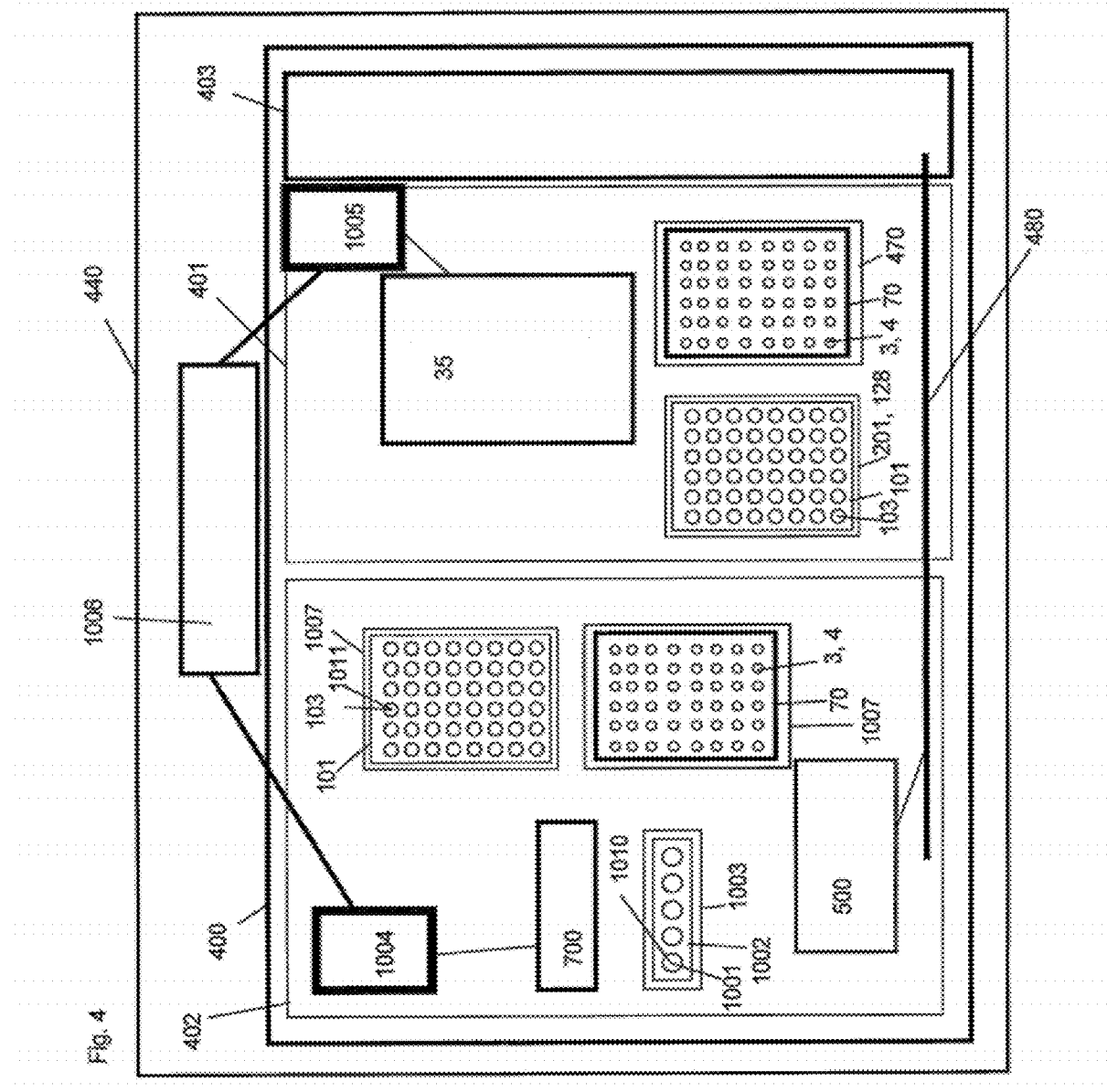

FIG. 4: Analytical system with control unit

Figure 5:
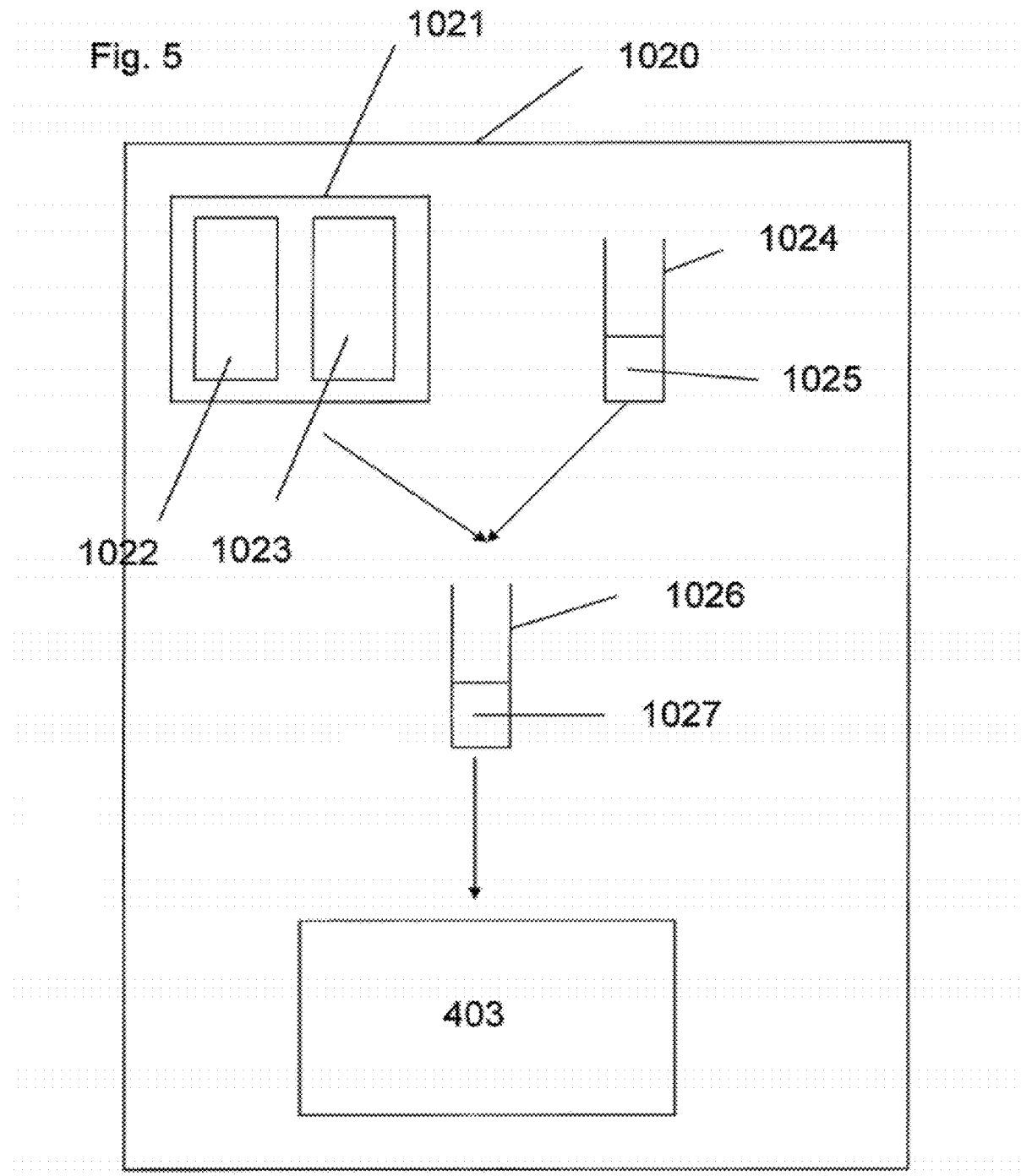

FIG. 5: System comprising kit with containers containing solutions

FIG. 6: System and process comprising solutions transferred to a container that is loaded onto an analyzer

DETAILED DESCRIPTION OF THE INVENTION

The present invention relates to a process for amplifying at least a first and a second target nucleic acid that may be present in at least one fluid sample. This process comprises separately incubating in at least two reaction vessels the nucleic acids with a solution comprising amplification reagents, and oligonucleotides specific for the first or second target nucleic acid, wherein the amplification reagents comprise a polymerase with reverse transcriptase activity, for a period of time and under conditions suitable for transcription of RNA by the polymerase with reverse transcriptase activity to occur. Following this first incubation, the target nucleic acids are incubated separately in the at least two reaction vessels with the solution comprising amplification reagents, and oligonucleotides specific for the first or second target nucleic acid for a period of time and under conditions sufficient for an amplification reaction indicative of the presence or absence of the first and second target nucleic acid to occur.

In the process, the solution in the first and in the second reaction vessels comprises the same proportion of amplification reagents. Oligonucleotides for the first target nucleic acid are present in the first of the at least two reaction vessels and absent in the second of the at least two reaction vessels, and oligonucleotides for the second target nucleic acid are present in the second of the at least two reaction vessels and absent in the first of the at least two reaction vessels.

One advantage of the present invention is that a single solution can be used to amplify different nucleic acids with sufficient efficiency. This simplifies assay development since only nucleic acids (i.e. oligonucleotides and/or control nucleic acids) need to be optimized. Optimization is understood to include sequence optimization, optimization of modifications of the nucleic acids and/or optimization of concentration in an assay.

One method of nucleic acid amplification is the Polymerase Chain Reaction (PCR) which is disclosed, among other references, in U.S. Pat. Nos. 4,683,202, 4,683,195, 4,800,159, and 4,965,188. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the target nucleic acids. A primer can be purified from a restriction digest by conventional methods, or it can be produced synthetically. The primer is usually single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have e.g. been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating, the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 5 sec to 9 min. In order to not expose the respective polymerase like e.g. the Z05 DNA Polymerase to such high temperatures for too long and thus risking a loss of functional enzyme, short denaturation steps are used usually.

In one embodiment of the invention, the time for the denaturation step is up to 30 sec, up to 20 sec, up to 10 sec, up to 5 sec, or about 5 sec. If the double-stranded template nucleic acid is denatured by heat, the reaction mixture is allowed to cool to a temperature that promotes annealing of each primer to its target sequence on the target nucleic acids.

The temperature for annealing is from about 35° C. to about 70° C., or from about 45° C. to about 65° C.; or from about 50° C. to about 60° C., or from about 55° C. to about 58° C. Annealing times can be from about 10 sec to about 1 min (e.g., about 20 sec to about 50 sec; about 30 sec to about 40 sec). In this context, it can be advantageous to use different annealing temperatures in order to increase the inclusivity of the respective assay. In brief, this means that at relatively low annealing temperatures, primers may also bind to targets having single mismatches, so variants of certain sequences can also be amplified. This can be desirable if e.g. a certain organism has known or unknown genetic variants which should also be detected. On the other hand, relatively high annealing temperatures bear the advantage of providing higher specificity, since towards higher temperatures the probability of primer binding to not exactly matching target sequences continuously decreases. In order to benefit from both phenomena, in some embodiments of the invention it is advantageous that the process described above comprises annealing at different temperatures, or first at a lower, then at a higher temperature. If, e.g., a first incubation takes place at 55° C. for about 5 cycles, non-exactly matching target sequences may be (pre-)amplified. This can be followed e.g. by about 45 cycles at 58° C., providing for higher specificity throughout the major part of the experiment. This way, potentially important genetic variants are not missed, while the specificity remains relatively high.

The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 60° C.). Extension times can be from about 10 sec to about 5 min, or about 15 sec to 2 min, or about 20 sec to about 1 min, or about 25 sec to about 35 sec. The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acids. The limiting factors in the reaction are the amounts of primers, thermostable enzyme, and nucleoside triphosphates present in the reaction. The cycling steps (i.e., denaturation, annealing, and extension) are repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Within the scope of the invention, PCR can be carried out in which the steps of annealing and extension are performed in the same step (one-step PCR) or, as described above, in separate steps (two-step PCR). Performing annealing and extension together and thus under the same physical and chemical conditions, with a suitable enzyme such as, for example, the Z05 DNA polymerase, bears the advantage of saving the time for an additional step in each cycle, and also abolishing the need for an additional temperature adjustment between annealing and extension. Thus, the one-step PCR reduces the overall complexity of the respective assay.

In general, shorter times for the overall amplification are better, as the time-to-result is reduced and leads to a possible earlier diagnosis.

Other nucleic acid amplification methods to be used in the context of the invention comprise the Ligase Chain Reaction (LCR; Wu D. Y. and Wallace R. B., Genomics 4 (1989) 560-69; and Barany F., Proc. Natl. Acad. Sci. USA 88 (1991) 189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), including real-time TMA, and Qβ-amplification (for a review see e.g. Whelen A. C. and Persing D. H., Annu. Rev. Microbiol. 50(1996) 349-373; Abramson R. D. and Myers T. W., Curr Opin Biotechnol 4 (1993) 41-47).

Suitable nucleic acid detection methods are known to the expert in the field and are described in standard textbooks as Sambrook J. et al., Molecular Cloning: A Laboratory Manual, Cold Spring Harbor Laboratory Press, Cold Spring Harbor, N.Y., 1989 and Ausubel F. et al.: Current Protocols in Molecular Biology 1987, J. Wiley and Sons, NY. There may be also further purification steps before the nucleic acid detection step is carried out as e.g. a precipitation step. The detection methods may include but are not limited to the binding or intercalating of specific dyes as ethidium bromide which intercalates into the double-stranded DNA and changes its fluorescence thereafter. The purified nucleic acid may also be separated by electrophoretic methods optionally after a restriction digest and visualized thereafter. There are also probe-based assays which exploit the oligonucleotide hybridization to specific sequences and subsequent detection of the hybrid.

The amplified target nucleic acids can be detected during or after the amplification reaction in order to evaluate the result of the analysis. Particularly for detection in real time, it is advantageous to use nucleic acid probes.

By using commercially available real-time PCR instrumentation (e.g., LightCycler™ or TaqMan®), PCR amplification and detection of the amplification product can be combined in a single closed cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory. However, other detection methods known to the skilled person may also be used.

The "first target nucleic acid" and the "second target nucleic acid" are different nucleic acids.

The term "fluid sample" as used herein comprises any fluid material that can be subjected to a diagnostic assay targeting nucleic acids and is usually derived from a biological source. In some embodiments, said fluid sample is derived from a human and is a body liquid. In one embodiment of the invention, the fluid sample is human blood, urine, sputum, sweat, swab, pipettable stool, or spinal fluid.

The term "reaction vessels" as used herein relates, but is not limited to, tubes or the wells of plates such as microwell, deepwell or other types of multiwell plates, in which a reaction for the analysis of the fluid sample such as e.g. reverse transcription or a polymerase chain reaction takes place. The outer limits or walls of such vessels are chemically inert such that they do not interfere with the analytical reaction taking place within. The isolation of the nucleic acids as described above is also carried out in a multiwell plate.

In this context, multiwell plates in analytical systems allow parallel separation and analyzing or storage of multiple samples. Multiwell plates may be optimized for maximal liquid uptake, or for maximal heat transfer. One embodiment of a multiwell plate for use in the context of the present invention is optimized for incubating or separating an analyte in an automated analyzer. Another multiwell plate is constructed and arranged to contact a magnetic device and/or a heating device. Embodiments of multiwell plates are further described hereinafter.

A "nucleic acid" as well as the "target nucleic acid" is a polymeric compound of nucleotides as known to the expert skilled in the art. "Target nucleic acid" is used herein to denote a nucleic acid in a sample which should be analyzed, i.e. the presence, non-presence and/or amount thereof in a sample should be determined.

According to the invention, an "oligomeric compound" is a compound consisting of "monomeric units" which may be nucleotides alone or non-natural compounds (see below), more specifically modified nucleotides (or nucleotide analogs) or non-nucleotide compounds, alone or combinations thereof.

"Oligonucleotides" and "modified oligonucleotides" (or "oligonucleotide analogs") are subgroups of oligomeric compounds. In the context of this invention, the term "oligonucleotide" refers to components formed from a plurality of nucleotides as their monomeric units. The phosphate groups are commonly referred to as forming the internucleoside backbone of the oligonucleotide. The normal linkage or backbone of RNA and DNA is a 3' to 5' phosphodiester linkage. Oligonucleotides and modified oligonucleotides (see below) useful for the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang S. A. et al., Methods in Enzymology 68 (1979) 90-98, the phosphodiester method disclosed by Brown E. L., et al., Methods in Enzymology 68 (1979) 109-151, the phosphoramidite method disclosed in Beaucage et al., Tetrahedron Letters 22 (1981) 1859, the H-phosphonate method disclosed in Garegg et al., Chem. Scr. 25 (1985) 280-282 and the solid support method disclosed in U.S. Pat. No. 4,458,066.

In the process according to the invention, the oligonucleotides may be chemically modified, i.e. the primer and/or the probe comprise a modified nucleotide or a non-nucleotide compound. The probe or the primer can then be a modified oligonucleotide.

The term "amplification reagents" as used herein relate to chemical or biochemical components that enable the amplification of nucleic acids. Such reagents comprise, but are not limited to, nucleic acid polymerases, buffers, mononucleotides such as nucleoside triphosphates, oligonucleotides e.g. as oligonucleotide primers, salts and their respective solutions, detection probes, dyes, and more.

In one embodiment of the invention, the solution in the first and in the second reaction vessels comprises the same concentration of amplification reagents. In another embodiment, any one of the target nucleic acids is simultaneously amplified with the other target nucleic acids in the process described herein. This is advantageous because multiple targets can be analyzed in parallel, increasing flexibility and throughput. In still another embodiment, any one of the target nucleic acids is amplified efficiently by the method hereinbefore described. This makes it possible to increase the throughput and flexibility of diagnostic testing.

"Simultaneously", in the sense of the invention, means that two actions, such as amplifying a first and a second or more nucleic acids, are performed at the same time and under the same physical conditions. In one embodiment of the invention, simultaneous amplification of the at least first and second target nucleic acids is performed in one vessel. In another embodiment, simultaneous amplification is performed with at least one nucleic acid in one vessel and at least a second nucleic acid in a second vessel, at the same time and under the same physical conditions, particularly with respect to temperature and incubation time.

"Limit of detection" or "LOD" means the lowest detectable amount or concentration of a nucleic acid in a sample. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is copy of the respective nucleic acid. IU/ml stands for "International units/ml", referring to the WHO standard.

Thus, in one embodiment, the process of the invention described above provides an LOD of 1 to 100 cp/ml or 0.5 to 50 IU/ml, or of 1 to 75 cp/ml or 0.5 to 30 IU/ml, or of 1 to 25 cp/ml or 1 to 20 IU/ml. Such LODs are necessary to have sufficiently sensitive tests for diagnostic purposes.

A widely used method for calculating an LOD is "Probit Analysis", which is a method of analyzing the relationship between a stimulus (dose) and the quantal (all or nothing) response. In a typical quantal response experiment, groups of animals are given different doses of a drug. The percent dying at each dose level is recorded. These data may then be analyzed using Probit Analysis. The Probit Model assumes that the percent response is related to the log dose as the cumulative normal distribution. That is, the log doses may be used as variables to read the percent dying from the cumulative normal. Using the normal distribution, rather than other probability distributions, influences the predicted response rate at the high and low ends of possible doses, but has little influence near the middle.

The Probit Analysis can be applied at distinct "hitrates". As known in the art, a "hit rate" is commonly expressed in percent [%] and indicates the percentage of positive results at a specific concentration of an analyte. Thus for example, an LOD can be determined at 95% hitrate, which means that the LOD is calculated for a setting in which 95% of the valid results are positive.

With respect to some examples of possible target nucleic acids from certain viruses, in one embodiment, the method according to the invention provides the following LODs:
  HIV: up to 60 cp/ml, or up to 50 cp/ml, or up to 40 cp/ml, or up to 30 cp/ml, or up to 20 cp/ml, or up to 15 cp/ml
  HBV: up to 10 IU/ml, or up to 7.5 IU/ml, or up to 5 IU/ml
  HCV: up to 10 IU/ml, or up to 7.5 IU/ml, or up to 5 IU/ml
  WNV I: up to 20 cp/ml, or up to 15 cp/ml, or up to 10 cp/ml
  WNV II: up to 20 cp/ml, or up to 15 cp/ml, or up to 10 cp/ml, or up to 5 cp/ml
  JEV: up to 100 cp/ml, or up to 75 cp/ml, or up to 50 cp/ml, or up to 30 cp/ml
  SLEV: up to 100 cp/ml, or up to 75 cp/ml, or up to 50 cp/ml, or up to 25 cp/ml, or up to 10 cp/ml.

Assays with LODs as hereinbefore described have the advantage that they can be used for in-vitro diagnostic tests. Higher LODs are not sufficiently sensitive. Thus, one particular advantage of the present invention is that a simplified process for amplification of target nucleic acids suitable for in-vitro diagnostics can be provided which comprises a generic solution which can be used for amplification different target nucleic acids as described herein with an LOD as described hereinbefore.

In one embodiment of the invention, the target nucleic acids are RNA. RNAs comprise, but are not limited to, viral RNA. Non-limiting examples are disclosed herein. In another embodiment, the target nucleic acids are DNA. DNAs comprise viral or bacterial DNA. Non-limiting examples are described herein. In still another embodiment, the first and said second target nucleic acids are enriched.

The term "enriched" as used herein relates to any method of treating a sample comprising a target nucleic acid that allows to separate the target nucleic acid from at least a part of other material present in the sample. "Enrichment" can, thus, be understood as a production of a higher amount of target nucleic acid over other material.

There are several methods for the purification of nucleic acids:
sequence-dependent or biospecific methods as e.g.:
affinity chromatography
hybridization to immobilized probes
sequence-independent or physico-chemical methods as e.g.:
liquid-liquid extraction with e.g. phenol-chloroform
precipitation with e.g. pure ethanol
extraction with filter paper
extraction with micelle-forming agents as cetyl-trimethyl-ammonium-bromide
binding to immobilized, intercalating dyes, e.g. acridine derivatives
adsorption to silica gel or diatomic earths
adsorption to magnetic glass particles (MGP) or organosilane particles under chaotropic conditions One method for enriching target nucleic acid is enrichment using Puregene-Kits commercially available from Qiagen (e.g order number 158389).

A "polymerase with reverse transcriptase activity" is a nucleic acid polymerase capable of synthesizing DNA based on an RNA template. It is also capable of the formation of a double-stranded DNA once the RNA has been reverse transcribed into a single strand cDNA. In one embodiment of the invention, the polymerase with reverse transcriptase activity is thermostable.

In one embodiment, the process according to the invention comprises incubating a sample containing an RNA template with an oligonucleotide primer sufficiently complementary to said RNA template to hybridize with the latter, and, in one embodiment, a thermostable DNA polymerase in the presence of at least all four natural or modified deoxyribonucleoside triphosphates, in an appropriate buffer comprising a metal ion buffer which buffers both the pH and the metal ion concentration. This incubation is performed at a temperature sufficient for said primer to hybridize to said RNA template and said DNA polymerase to catalyze the polymerization of said deoxyribonucleoside triphosphates to form a cDNA sequence complementary to the sequence of said RNA template.

As used herein, the term "cDNA" refers to a complementary DNA molecule synthesized using a ribonucleic acid strand (RNA) as a template. The RNA may e.g. be mRNA, tRNA, rRNA, or another form of RNA, such as viral RNA. The cDNA may be single-stranded, double-stranded or may be hydrogen-bonded to a complementary RNA molecule as in an RNA/cDNA hybrid.

A primer suitable for annealing to an RNA template may also be suitable for amplification by PCR. For PCR, a second primer, complementary to the reverse transcribed cDNA strand, provides an initiation site for the synthesis of an extension product.

In the amplification of an RNA molecule by a DNA polymerase, the first extension reaction is reverse transcription using an RNA template, and a DNA strand is produced. The second extension reaction, using the DNA template, produces a double-stranded DNA molecule. Thus, synthesis of a complementary DNA strand from an RNA template by a DNA polymerase provides the starting material for amplification.

Thermostable DNA polymerases can be used in a coupled, one-enzyme reverse transcription/amplification reaction. The term "homogeneous", in this context, refers to a two-step single addition reaction for reverse transcription and amplification of an RNA target. By homogeneous it is meant that following the reverse transcription (RT) step, there is no need to open the reaction vessel or otherwise adjust reaction components prior to the amplification step. In a non-homogeneous RT/PCR reaction, following reverse transcription and prior to amplification one or more of the reaction components such as the amplification reagents are e.g. adjusted, added, or diluted, for which the reaction vessel has to be opened, or at least its contents have to be manipulated. While both homogeneous and non-homogeneous embodiments are comprised by the scope of the invention, the homogeneous format for RT/PCR advantageous.

Reverse transcription is an important step in RT/PCR. It is, for example, known in the art that RNA templates show a tendency towards the formation of secondary structures that may hamper primer binding and/or elongation of the cDNA strand by the respective reverse transcriptase. Thus, relatively high temperatures for an RT reaction are advantageous with respect to efficiency of the transcription. On the other hand, raising the incubation temperature also implies higher specificity, i.e. the RT primers will not anneal to sequences that exhibit mismatches to the expected sequence or sequences. Particularly in the case of multiple different target RNAs, it can be desirable to also transcribe and subsequently amplify and detect sequences with single mismatches, e.g. in the case of the possible presence of unknown or rare substrains or subspecies of organisms in the fluid sample.

In order to benefit from both advantages described above, i.e. the reduction of secondary structures and the reverse transcription of templates with mismatches, it is one aspect of the invention to carry out the RT incubation at more than one different temperature.

Therefore, one aspect of the invention is the process described above, wherein the incubation step of the polymerase with reverse transcriptase activity is carried out at different temperatures from 30° C. to 75° C., or from 45° C. to 70° C., or from 55° C. to 65° C.

As a further important aspect of reverse transcription, long RT steps can damage the DNA templates that may be present in the fluid sample. If the fluid sample contains both RNA and DNA species, it is thus favorable to keep the duration of the RT steps as short as possible, but at the same time ensuring the synthesis of sufficient amounts of cDNA for the subsequent amplification and optional detection of amplificates.

Thus, one aspect of the invention is the process described above, wherein in the incubation step for transcription of RNA, the period of time is up to 30 minutes, 20 minutes, 15 minutes, 12.5 minutes, 10 minutes, 5 minutes, or 1 minute.

A further aspect of the invention is the process described above, wherein the polymerase with reverse transcriptase activity and comprising a mutation is selected from the group consisting of
a. a CS5 DNA polymerase
b. a CS6 DNA polymerase
c. a *Thermotoga maritima* DNA polymerase
d. a *Thermus aquaticus* DNA polymerase
e. a *Thermus thermophilus* DNA polymerase
f. a *Thermus flavus* DNA polymerase
g. a *Thermus filiformis* DNA polymerase
h. a *Thermus* sp. sps17 DNA polymerase
i. a *Thermus* sp. Z05 DNA polymerase
j. a *Thermotoga neapolitana* DNA polymerase
k. a *Termosipho africanus* DNA polymerase
l. a *Thermus caldophilus* DNA polymerase Particularly suitable for these requirements are enzymes carrying a mutation in the polymerase domain that enhances their reverse transcription efficiency in terms of a faster extension rate.

Therefore, one aspect of the invention is the process described above, wherein the polymerase with reverse transcriptase activity is a polymerase comprising a mutation conferring an improved nucleic acid extension rate and/or an improved reverse transcriptase activity relative to the respective wildtype polymerase.

In one embodiment, in the process described above, the polymerase with reverse transcriptase activity is a polymerase comprising a mutation conferring an improved reverse transcriptase activity relative to the respective wildtype polymerase.

Polymerases carrying point mutations that render them particularly useful in the context of the invention are disclosed in WO 2008/046612. Advantageous polymerases to be used in the context of the present invention are mutated DNA polymerases comprising at least the following motif in the polymerase domain:
T-G-R-L-S—S—$X_{b7}$—$X_{b8}$—P—N-L-Q-N; wherein $X_{b7}$ is an amino acid selected from S or T and wherein $X_{b8}$ is an amino acid selected from G, T, R, K, or L, wherein the polymerase comprises 3'-5' exonuclease activity and has an improved nucleic acid extension rate and/or an improved reverse transcription efficiency relative to the wildtype DNA polymerase, wherein in said wildtype DNA polymerase $X_{b8}$ is an amino acid selected from D, E or N.

One example is mutants of the thermostable DNA polymerase from *Thermus* species Z05 (described e.g. in U.S. Pat. No. 5,455,170), said mutatnts comprising mutations in the polymerase domain as compared with the respective wildtype enzyme Z05. One mutant for the method according to the invention is a mutant Z05 DNA polymerase wherein the amino acid at position 580 is selected from the group consisting of G, T, R, K and L.

Since it is in the scope of the invention to reverse-transcribe RNA target nucleic acids into cDNA while preserving the DNA target nucleic acids so both cDNA and DNA can be used for subsequent amplification, the process according to the invention is particularly useful for the simultaneous amplification of target nucleic acids derived from both organisms having an RNA or organisms having a DNA genome. This advantage considerably increases the spectrum of different organisms, especially pathogens that can be analyzed under identical physical conditions.

Therefore, one aspect of the invention is the process described above, wherein the at least two target nucleic acids comprise RNA and DNA.

Especially due to an appropriate temperature optimum, enzymes like Tth polymerase or, the mutant Z05 DNA polymerase mentioned above are suited to carry out the subsequent step of amplification of the target nucleic acids. Exploiting the same enzyme for both reverse transcription an amplification contributes to the ease of carrying out the process and facilitates its automation, since the fluid sample does not have to be manipulated between the RT and the amplification step.

Therefore, in one embodiment, in the process described above the same polymerase with reverse transcriptase activity is used in step d) and step e). In one embodiment, the enzyme is the mutant Z05 DNA polymerase described supra.

In order not to expose the polymerase or other components of the reaction mixture used in the context of the invention to elevated temperatures for a longer time than necessary, in one embodiment, steps above 90° C. are carried out in time periods of up to 20 sec, or up to 15 sec, or up to 10 sec, or up to 5 sec and or 5 sec. This also reduces the time-to-result and cuts down the overall required time of the assay.

In such a homogeneous setup, it can be of considerable advantage to seal the reaction vessels prior to initiating the RT and the amplification, thereby reducing the risk of contamination. Sealing can be e.g. achieved by applying a foil that is transparent, a cap, or by oil added to the reaction vessels and forming a lipophilic phase as a sealing layer at the top of the fluid.

Thus, one aspect of the invention is the process described above, further comprising between the step of purifying the nucleic acids and the steps of RT and amplification, the step of sealing the at least two reaction vessels.

The target of the amplification step can be an RNA/DNA hybrid molecule. The target can be a single-stranded or double-stranded nucleic acid. Although the most widely used PCR procedure uses a double-stranded target, this is not a necessity. After the first amplification cycle of a single-stranded DNA target, the reaction mixture contains a double-stranded DNA molecule consisting of the single-stranded target and a newly synthesized complementary strand. Similarly, following the first amplification cycle of an RNA/cDNA target, the reaction mixture contains a double-stranded cDNA molecule. At this point, successive cycles of amplification proceed as described above.

Since nucleic acid amplification, especially but not only in the case of PCR, is very efficient if carried out as a cycling reaction, one aspect of the invention is the process described above, wherein the amplification reaction consists of multiple cycling steps.

In the sample preparation steps following the lysis step, the component of interest is further enriched. If the non-proteinaceous components of interest are e.g. nucleic acids, they are normally extracted from the complex lysis mixtures before they are used in a probe-based assay.

In one embodiment, in the process hereinbefore described, the transcription and amplification steps are preceded by the following steps. A plurality of vessels comprising different types of fluid samples is provided. A solid support material is combined together with the plurality of different types of fluid samples in vessels for a period of time and under conditions sufficient to permit nucleic acids comprising the target nucleic acids to be immobilized on the solid support material. The solid support material is then isolated from the other material present in the fluid samples in a separation station, and the nucleic acids are purified in a separation station by separating the fluid sample from the solid support material and washing the solid support material one or more times with a wash buffer. The physical conditions and the period of time of the combining of the solid support material and the plurality of different types of fluid samples are identical for any one of the plurality of different types of fluid samples.

In the sense of the invention, "purification", "isolation" or "extraction" of nucleic acids relate to the following: Before nucleic acids may be analyzed in a diagnostic assay e.g. by amplification, they typically have to be purified, isolated or extracted from biological samples containing complex mixtures of different components. For the first steps, processes may be used which allow the enrichment of the nucleic acids. Such methods of enrichment are described herein.

A "wash buffer" is a fluid that is designed to remove undesired components, especially in a purification procedure. Such buffers are well known in the art. In the context of the purification of nucleic acids, the wash buffer is suited to wash the solid support material in order to separate the immobilized nucleic acid from any unwanted components. The wash buffer may, for example, contain ethanol and/or chaotropic agents in a buffered solution or solutions with an acidic pH without ethanol and/or chaotropic agents as described above. Often the washing solution or other solutions are provided as stock solutions which have to be diluted before use.

The washing in the process according to the invention requires a more or less intensive contact of the solid support material and the nucleic acids immobilized thereon with the wash buffer. Different methods are possible to achieve this, e.g. shaking the wash buffer with the solid support material in or along with the respective vessel or vessels. Another advantageous method is aspirating and dispensing the suspension comprising wash buffer and solid support material one or more times. This method is, in one embodiment, carried out using a pipet, wherein said pipet comprises a disposable pipet tip into which said suspension is aspirated and from which it is dispensed again. Such a pipet tip can be used several times before being discarded and replaced. Disposable pipet tips useful for the invention have a volume of at least 10 or at least 15 µl, or at least 100 or at least 500 or of at least 1 ml, or of about 1 ml. Pipets used in the context of the invention can also be pipetting needles.

Thus, one aspect of the invention is the process described above, wherein a washing step comprises aspirating and dispensing the wash buffer comprising the solid support material.

Especially, but not only for clinical laboratories with a high sample throughput, it is highly favorable to be provided with such an improved method for the quick, easy and reliable simultaneous isolation of multiple target nucleic acids from a plurality of different types of fluid samples.

The process comprising the automated steps mentioned above displays various advantages. Firstly, the combination of the sample preparation procedure according to the present invention with e.g. reverse transcription of RNA and amplification of the target nucleic acids in an automated manner significantly reduces the need for manual intervention and thereby the potential risk of contamination.

Moreover, the possibility of providing a single process in which a variety of different samples, i.e. different sources of nucleic acids, contributes significantly to reduction of the overall complexity of nucleic acid diagnostics. If, for example, different methods have to be applied to every type of fluid sample, as it has been the case in the prior art, sample preparation is much more complex, time-consuming and resource-intensive. Mostly, different reagents have to be exploited, leading to increased costs and hampering the development of quick and uncomplicated automated solutions.

The sample preparation according to the invention exhibits the appropriate flexibility and workflow to deal with multiple different sample types containing different types of nucleic acids such as for example DNA and RNA.

The process according to the invention requires considerably less hands-on time and testing is much simpler to perform than sample preparation methods used in the prior art. The process according to the invention offers a major advantage e.g. in the field of clinical virology as it permits parallel sample preparation and downstream amplification of several viruses in parallel experiments.

Therefore, one aspect of the invention is the process described supra, further comprising a step for releasing nucleic acids from their cellular and/or viral environment by lysing cells and/or viral capsids potentially present in the plurality of different fluid samples.

To release the contents of cells or viral particles, they may be treated with enzymes or with chemicals to dissolve, degrade or denature the cellular walls or viral particles. This process is commonly referred to as lysis. The resulting solution containing such lysed material is referred to as lysate.

Often, the nucleic acids to be analyzed are not free in solution within the fluid sample in question, but are located within closed structures such as for example cells or viruses. In diagnostic assays it is often the objective to identify especially pathogenic cells or viruses in fluid samples such as clinical samples. Such pathogens can e.g. comprise RNA viruses like for example Human Immunodeficiency Virus (HIV), Hepatitis C Virus (HCV), the West Nile Virus (WNV), Human Papilloma Virus (HPV), Japanese Encephalitis Virus (JEV), St. Louis Encephalitis Virus (SLEV) and others, or DNA viruses like e.g. Hepatitis B Virus (MC), Cytomegalovirus (CMV) and others, or bacteria like e.g. *Chlamydia trachomatis* (CT), *Neisseria gonorrhoeae* (NG) and others. The method according to the invention is useful for the extraction of nucleic acids from the above-mentioned as well as other organisms.

Agents suitable to lyse cells and/or viral capsids or similar structures are commonly provided within a lysis buffer. Hence, in one embodiment of the invention, the process described above further comprises a step for the addition of a lysis buffer to the plurality of different fluid samples.

Since the process according to the invention is especially advantageous with respect to high throughput, efficiency and parallelization, one aspect of the invention is the process described above, wherein said lysis buffer is identical for the members of said plurality of different types of fluid samples.

This way, the complexity of the sample preparation procedure is further reduced, since no different lysis reagents have to be provided individually for the different samples to be treated. Furthermore, the procedure can be controlled more easily when working with a single lysis buffer. The lysis buffer can e.g. be withdrawn with a mulipipettor from a single container and subsequently be dispensed into the different samples simultaneously.

In one embodiment of the invention, the lysis buffer in the process described above comprises one or more components selected from the group of:
  a chaotropic agent
  a buffer substance
  an alcohol
  a reducing agent.

Chaotropic agents, which generally disturb the ordered structure of water molecules in solution and non-covalent binding forces in and between molecules, can make several contributions to the procedure of sample preparation. In particular, but not only, they can be applied as RNase inhibitors by disturbing the nuclease's tertiary structure. Usually, no further RNase inhibitor has to be applied to the lysis buffer. Besides, chaotropic agents contribute to the disruption of biological membranes, such as plasma membranes or the membranes of cell organelles if present. Also, they can play a significant role in the adhesive binding of nucleic acids to surfaces like glass (see infra). Chaotropic agents in the context of the invention are guanidinium salts like guanidinium thiocyanate or guanidinium hydrochloride or guanidinium chloride or guanidinium isothiocyanate, urea, perchlorates such as e.g. potassium perchlorate, other thiocyanates or potassium iodide. However, other chaotropic agents can also be used within the scope of the invention.

Buffer substances are generally important for maintaining a certain pH value or pH range in a solution. This is the prerequisite for most biological systems, and mostly also desirable for in vitro reactions. It can also be advantageous for the process of the invention. Buffers in the context of the lysis buffer are citrate buffers such as sodium citrate, but also Tris (Tris-(hydroxymethyl)-aminomethane) buffers such as Tris HCl, phosphate, N-(2-hydroxyethyl)-piperazine-N'-(2-ethanesulfonic acid) (HEPES), acetate buffers, but also other buffers can be used in the context of the invention.

The use of alcohol in a lysis buffer for nucleic acid preparation can also be advantageous, as known by the person skilled in the art. One alcohol of use is polidocanol, while other alcohols may also be used in the lysis buffer described above. The use of polidocanol for the preparation of nucleic acids has e.g. been described in EP 1 932 913.

Reducing agents can also contribute to the denaturation of undesired components such as the RNase A mentioned above. In particular, reducing agents, as widely known in the art, cleave inter- and intramolecular disulfide bonds, which are especially important for the tertiary structure of many proteins. Embodimnts in the context of the invention are reducing agents such as dithiothreitol (DTT), but other reducing agents known in the art such as e.g. 2-mercaptoethanol can also be advantageously employed in the context of the invention.

In view of the aforementioned, one aspect of the invention is the process described above, wherein said lysis buffer comprises the following components:
Guanidinium thiocyanate,
NaCitrate,
polydocanol,
DTT.

In one embodiment of the invention, the concentrations of the above-mentioned components of the lysis buffer are as follows
Guanidinium thiocyanate: 4 M
NaCitrate: 50 mM
polydocanol: 5% w/v
DTT: 2% w/v.

The pH of the lysis buffer described above is not restricted to specific pH values. However, in one embodiment, said lysis buffer has an acidic pH, or a pH between 5.5 and 6.5, or about 5.8.

Enzymes which are used in such lysis or sample preparation processes mentioned above are enzymes which cleave the amide linkages in protein substrates and which are classified as proteases, or (interchangeably) peptidases (see Walsh, 1979, Enzymatic Reaction Mechanisms. W. H. Freeman and Company, San Francisco, Chapter 3). Proteases used in the prior art comprise alkaline proteases (WO 98/04730) or acid proteases (U.S. Pat. No. 5,386,024). A protease which has been widely used for sample preparation in the isolation of nucleic acids in the prior art is proteinase K from Tritirachium album (see e.g. Sambrook J. et al., Molecular Cloning: A Laboratory Manual, Cold Spring Harbor Laboratory Press, Cold Spring Harbor, N.Y., 1989) which is active around neutral pH and belongs to a family of proteases known to the person skilled in the art as subtilisins. Useful in lysis or sample preparation processes mentioned above is the enzyme esperase, a robust protease that retains its activity at both high alkalinity and at high temperatures.

Particularly interesting for purification purposes is the adsorption of nucleic acids to a glass surface although other surfaces are possible. Many procedures for isolating nucleic acids from their natural environment have been proposed in recent years by the use of their binding behavior to glass surfaces. If unmodified nucleic acids are the target, a direct binding of the nucleic acids to a material with a silica surface is advantageous because, among other reasons, the nucleic acids do not have to be modified, and even native nucleic acids can be bound. These processes are described in detail by various documents. In Vogelstein B. et al., Proc. Natl. Acad. USA 76 (1979) 615-9, for instance, a procedure for binding nucleic acids from agarose gels in the presence of sodium iodide to ground flint glass is proposed. The purification of plasmid DNA from bacteria on glass dust in the presence of sodium perchlorate is described in Marko M. A. et al., Anal. Biochem. 121 (1982) 382-387. In DE-A 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Jakobi R. et al., Anal. Biochem. 175 (1988) 196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples. Magnetic, porous glass is also commercially available that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic pigments are used for this purpose. Magnetic glass particles and methods using them are those described in WO 01/37291.

The flexibility of the process according to the invention can be further improved by adapting the volume of the respective fluid sample used in the process. This embodiment focuses on the diversity of the different types of fluid samples and possibly the types of organisms and nucleic acids present within them. E.g., certain viruses in a whole blood sample may require more starting material than other samples, if it is known that usually only low copy numbers are present in these specific cases.

Thus, one aspect of the invention is the process described above, wherein at least one fluid sample of said plurality of different fluid samples has a different volume than the other fluid samples. In one embodiment, alternatively or additionally, different volumes of lysis buffer are added to said plurality of different fluid samples. In a further embodiment, when at least one fluid sample of said plurality of different fluid samples has a different volume than the other fluid samples, lysis buffer is added to the samples such that all samples have the same volume after addition. In this embodiment, it is even more convenient to carry out an automated process on the different samples simultaneously. The advantages of being able to choose an appropriate starting volume depending on the sample type and of having identical volumes for carrying out the isolation and optionally e.g. amplification and detection are combined in this approach.

The term "solid support material" comprises any of the solid materials mentioned above in connection with the immobilization of nucleic acids, e.g. magnetic glass particles, glass fibers, glass fiber filters, filter paper etc., while the solid support material is not limited to these materials.

One aspect of the invention is the process described above, wherein the solid support material comprises nucleic acid binding particles, or one or more of the materials selected from silica, metal, metal oxides, plastic, polymers and nucleic acids. In one embodiment of the invention, the solid support material is magnetic glass particles.

"Immobilize", in the context of the invention, means to capture objects such as e.g. nucleic acids in a reversible or irreversible manner. Particularly, "immobilized on the solid support material", means that the object or objects are associated with the solid support material for the purpose of their separation from any surrounding media, and can be recovered e.g. by separation from the solid support material at a later point. In this context, "immobilization" can e.g. comprise the adsorption of nucleic acids to glass or other suitable surfaces of solid materials as described supra. Moreover, nucleic acids can be "immobilized" specifically by binding to capture probes, wherein nucleic acids are bound to essentially complementary nucleic acids attached to a solid support by base-pairing. In the latter case, such specific immobilization leads to the predominant binding of target nucleic acids.

One embodiment of the process hereinbefore described comprises the step of contacting the purified nucleic acids with amplification reagents comprising a polymerase with reverse transcriptase activity in at least two reaction vessels, wherein at least a first reaction vessel comprises at least a first target nucleic acid and at least a second reaction vessel comprises at least a second target nucleic acid;

incubating in the reaction vessels the purified nucleic acids with the amplification reagents for a period of time and under conditions suitable for transcription of RNA by the polymerase with reverse transcriptase activity to occur.

In one embodiment of the process hereinbefore described, the conditions for the transcription step and the amplification step are identical for the at least first and second target nucleic acids comprised in the first and second reaction vessels.

In one aspect of the present invention, the first and the second nucleic acid are present in at least two fluid samples.

In another aspect of the present invention, the first and the second target nucleic acids are amplified simultaneously.

In one aspect of the present invention, the reaction mixture for amplifying the first target nucleic acid comprises an optimized concentration of oligonucleotides specific for the first target nucleic acid and the reaction mixture for amplifying the second target nucleic acid comprises an optimized concentration of the oligonucleotides specific for the second target nucleic acid.

In one aspect of the process described herein, the concentration of the oligonucleotides specific for the first target nucleic acid in the reaction mixture for amplifying the first target nucleic acid is substantially the same as the concentration of the oligonucleotides specific for the second target nucleic acid in the reaction mixture for amplifying the second target nucleic acid.

In one aspect of the invention described herein, the amplification reagents also comprise an internal control (IC) and/or an internal quantitative standard (QS). In one embodiment said IC and/or QS are comprised in the solution comprising the enzyme for amplification. In one embodiment of the present invention, the oligonucleotides for amplification of the internal control (IC) and/or internal quantitative standard (QS) are also comprised in said solution. In another embodiment of the present invention, the concentration of said internal control (IC) and/or internal quantitative standard (QS) are also optimized individually. In one embodiment, the sequence of the internal control and/or internal quantitative standard is identical for at least a first and a second target nucleic acid, or for more than two target nucleic acids. In a further embodiment, the sequence of the IC and the IQS are identical. This generic internal control (IC) and/or internal quantitative standard (QS) allows for the development of simultaneous assays on a plurality of parameters and/or nucleic acid types while using the same internal control nucleic acid sequence for said different parameters and/or nucleic acid types. Therefore, it contributes to reducing the overall complexity of the corresponding experiments on various levels: For instance, only one internal control nucleic acid sequence has to be designed and added to the respective amplification mixes, thus saving the time and costs for designing and synthesizing or buying multiple control nucleic acid sequences. The assay or assays can be streamlined, and the risk of handling errors is reduced. In addition, the more different control nucleic acid sequences are employed in one assay or parallel assays carried out simultaneously under the same conditions, the more complex it may result to adjust the respective conditions. Moreover, with a single control suitable for detection of a plurality of target nucleic acids, said control can be dispensed from a single source e.g. into different vessels containing said different target nucleic acids. Within the scope of the invention, the single control nucleic acid sequence may also serve as a qualitative and as a quantitative control. Internal control sequences are selected from the group comprising Seq ID No. 45 to 48.

As a further advantage of the control described above, the testing of a particular biological sample for other nucleic acids in possible subsequent experiments need not involve another sample preparation procedure with the addition of a different internal control nucleic acid, since the control used in the invention can be used to control the amplification of different nucleic acids. Thus, once an internal control nucleic acid has been added, other parameters may be tested in the same sample under the same conditions.

The internal control nucleic acid can be competitive, non-competitive or partially competitive. A competitive internal control nucleic acid carries essentially the same primer binding sites as the target and thus competes for the same primers with the target. While this principle allows a good mimicry of the respective target nucleic acid due to their similar structure, it can lower the amplification efficiency with regard to the target nucleic acid or acids and thus lead to a less sensitive assay.

A non-competitive internal control nucleic acid has different primer binding sites than the target and thus binds to different primers. Advantages of such a setup comprise, among others, the fact that the single amplification events of the different nucleic acids in the reaction mixture can take place independently from each other without any competition effects. Thus, no adverse effects occur regarding the limit of detection of the assay as can be the case in a competitive setup.

Finally, in an amplification reaction using a partially competitive setup the respective control nucleic acid and at least one of the target nucleic acids compete for the same primers, while at least one other target nucleic acid binds to different primers.

The fact that the method described above involves a distinct set of primers for each of the target nucleic acids and for the internal control nucleic acid renders the method considerably flexible. In this non-competitive setup it is not necessary to introduce target-specific binding sites into the control nucleic acid as in the case of a competitive setup, and the drawbacks of a competitive setup as mentioned above are avoided. In a non-competitive setup, the internal control nucleic acid has a sequence different from any target sequences, in order not to compete for their primers and/or probes. In one embodiment, the sequence of the internal control nucleic acid is different from the other nucleic acid sequences in the fluid sample. As an example, if the fluid sample is derived from a human, the internal control nucleic acid does not have a sequence which also endogenously occurs within humans. The difference in sequence should thus be at least significant enough to not allow the binding of primers and/or probes to the respective endogenous nucleic acid or acids under stringent conditions and thus render the setup competitive. In order to avoid such interference, the sequence of the internal control nucleic acid used in the invention is, in one embodiment, derived from a source different from the origin of the fluid sample. In one embodiment, it is derived from a naturally occurring genome. In one embodiment, it is derived from a plant genome, in a further embodiment from a grape genome. In one embodiment, a nucleic acid derived from a naturally occurring genome is scrambled. As known in the art, "scrambling" means introducing base mutations in a sequence to a certain extent. In one embodiment, the sequence of the internal control nucleic acid used in the invention is substantially altered with respect to the naturally occurring gene it is derived from. This has the advantage that crossreactivity of primers and probes with nucleic acids in the fluid samples is greatly reduced.

In one one embodiment, the IC/IQS is DNA. If the target nucleic acid is an RNA, the IC/IQS is RNA. If both RNA and DNA are to be analyzed in the process described supra, the internal control nucleic acid is RNA, as the internal control nucleic acid mimics the most sensitive target of an assay involving multiple targets, and RNA targets usually have to be more closely controlled. Since RNA is more prone to degradation than DNA due to influences such as alkaline pH, ribonucleases etc., internal control nucleic acids made of RNA are, in one embodiment, provided as armored particles. Armored particles such as especially armored RNA are described e.g. in EP910643. In brief, the RNA, which can be produced chemically or, in one embodiment, heterologously e.g. by bacteria such as e.g. *E. coli*, is at least partially encapsulated in a viral coat protein. The latter confers resistance of the RNA towards external influences, in particular ribonucleases. It must be understood that internal control DNA can also be provided as an armored particle. Both armored RNA and DNA are useful as internal control nucleic acids in the context of the invention. In one embodiment, RNA control nucleic acids are armored with the MS2 coat protein in *E. coli*. In a further embodiment, DNA control nucleic acids are armored using lambda phage GT11.

The process comprising the automated steps mentioned above also displays various additional advantages:

It has been a challenge in the prior art that the number of different target nucleic acids in a multiplex assay carried out in a single reaction vessel is limited by the number of appropriate labels. In a real-time PCR assay, for example, the potential overlap of fluorochrome spectra has a great impact on assay performance (risk of false positive results, lower precision etc.) Therefore, the respective fluorophores have to be carefully selected and spectrally well separated in order to assure the desired performance of a diagnostic test. Typically, the number of different usable fluorophores corresponds to a single-digit number of PCR instrument fluorescence channels.

In contrast, in the process described supra, the internally controlled amplification of at least a first and a second target nucleic acid takes place in at least two different reaction vessels, allowing for the simultaneous amplification of a higher number of different target nucleic acids, since signals in different reaction vessels can be detected independently from each other. This means that the first target nucleic acid is amplified in a first but not a second vessel, and the second target nucleic acid is amplified in the second but not the first vessel. Still, within the scope of the present invention are embodiments wherein in one or more of the multiple reaction vessels multiplex reactions are performed, thereby multiplying the number of targets that may be amplified simultaneously and under the same conditions. In such embodiments, the internal control nucleic acid serves as a control for the different target nucleic acids within a vessel as well as different target nucleic acids in different vessel.

Thus, one aspect of the invention relates to the process described supra, wherein at least two target nucleic acids are amplified in the same reaction vessel. In other cases, it may be convenient to amplify the first, but not the second target nucleic acid in the first reaction vessel, e.g. depending on the sample and/or the target nucleic acid or acids in question.

Therefore, one embodiment of the invention is the process described above, wherein the second target nucleic acid is absent from the first reaction vessel.

Especially if a fluid sample is suspected to contain target nucleic acids from different organisms, or even the different organisms as such, or if it is not clear which of the different nucleic acids or organisms may be present in said sample, one embodiment of the invention is the process described above, wherein the first target nucleic acid and the second target nucleic acid are from different organisms.

As described before, the process described above is useful for qualitatively or quantitatively controlling the amplification of at least a first and a second target nucleic acid.

Qualitative detection of a nucleic acid in a biological sample is crucial e.g. for recognizing an infection of an individual. Thereby, one important requirement for an assay for detection of a microbial infection is that false-negative or false-positive results be avoided, since such results would almost inevitably lead to severe consequences with regard to treatment of the respective patient. Thus, especially in PCR-based methods, a qualitative internal control nucleic acid is added to the detection mix. Said control is particularly important for confirming the validity of a test result: At least in the case of a negative result with regard to the respective target nucleic acid, the qualitative internal control reaction has to perform reactive within given settings, i.e. the qualitative internal control must be detected, otherwise the test itself is considered to be inoperative. However, in a qualitative setup, said qualitative internal control does not necessarily have to be detected in case of a positive result. For qualitative tests, it is especially important that the sensitivity of the reaction is guaranteed and therefore strictly controlled As a consequence, the concentration of the qualitative internal control must be relatively low so that even in a situation e.g. of slight inhibition the qualitative internal control is not be detected and therefore the test is invalidated.

Thus, one aspect of the invention is the process described above, wherein the presence of an amplification product of said internal control nucleic acid is indicative of an amplification occurring in the reaction mixture even in the absence of amplification products for one or more of said target nucleic acids.

On the other hand and in addition to mere detection of the presence or absence of a nucleic acid in a sample, it is often important to determine the quantity of said nucleic acid. As an example, stage and severity of a viral disease may be assessed on the basis of the viral load. Further, monitoring of any therapy requires information on the quantity of a pathogen present in an individual in order to evaluate the therapy's success. For a quantitative assay, it is necessary to introduce a quantitative standard nucleic acid serving as a reference for determining the absolute quantity of a target nucleic acid. Quantitation can be effectuated either by referencing to an external calibration or by implementing an internal quantitative standard.

In the case of an external calibration, standard curves are created in separate reactions using known amounts of identical or comparable nucleic acids. The absolute quantity of a target nucleic acid is subsequently determined by comparison of the result obtained with the analyzed sample with said standard function. External calibration, however, has the disadvantage that a possible extraction procedure, its varied efficacy, and the possible and often not predictable presence of agents inhibiting the amplification and/or detection reaction are not reflected in the control.

This circumstance applies to any sample-related effects. Therefore, it might be the case that a sample is judged as negative due to an unsuccessful extraction procedure or other sample-based factors, whereas the target nucleic acid to be detected and quantified is actually present in the sample.

For these and other reasons, an internal control nucleic acid added to the test reaction itself is of advantage. When serving as a quantitative standard, said internal control nucleic acid has at least the following two functions in a quantitative test:
i) It monitors the validity of the reaction.
ii) It serves as reference in titer calculation thus compensating for effects of inhibition and controlling the preparation and amplification processes to allow a more accurate quantitation. Therefore, in contrast to the qualitative internal control nucleic acid in a qualitative test which must be positive only in a target-negative reaction, the quantitative control nucleic acid in a quantitative test has two functions: reaction control and reaction calibration. Therefore it must be positive and valid both in target-negative and target-positive reactions.

It further has to be suited to provide a reliable reference value for the calculation of high nucleic acid concentrations. Thus, the concentration of an internal quantitative control nucleic acid needs to be relatively high.

In one embodiment of the present invention, the process is automated.

The present invention also relates to an analytical system for isolating and amplifying at least two different nucleic acids that may be present in at least one sample comprising
a separation station constructed and arranged to separate the nucleic acids from other material,
a kit comprising at least one container, the at least one container comprising a solution comprising amplification reagents,
a first solution comprising oligonucleotides for amplifying a first target nucleic acid,
a second solution comprising oligonucleotides for amplifying a second target nucleic acid,
an amplification station comprising reaction vessels,
wherein the solution comprising amplification reagents and the first or the second solution comprising oligonucleotides are combined such that said reaction vessels comprise amplification reagents, separated target nucleic acid and oligonucleotides, wherein the proportion of amplification reagents is identical in reaction vessels comprising oligonucleotides for amplifying the first target nucleic acid, and in reaction vessels comprising oligonucleotides for amplifying the second target nucleic acid.

Embodiments of this system are described hereinbefore and hereinafter. FIG. 5 shows one exemplary system (1020). This system comprises kit (1021) comprising containers (1022) and (1023), which comprise solutions (1028) and (1029). A container (1024) comprises a solution (1025) which is a solution containing oligonucleotides (1025). Solutions from the containers (1022) and/or (1023) are combined with solution (1025). This may be done either by adding solution (1025) to container (1022) or (1023), and then combining all solutions or by adding solution (1028) and/or (1029) into reaction vessel (1026), and then add solution (1025). It is understood that only the necessary volumes from containers (1022), (1023), (1024) are added to reaction vessel (1026), not all of their contents. After adding appropriate volumes to reaction vessel (1026), reaction vessel (1026) is incubated in amplification station (403). Embodiments of solutions, containers and vessels are as described herein.

One advantage of the system of the present invention is that it is not necessary to produce different bulk solutions comprising amplification reagents for amplifying different target nucleic acids efficiently, with the LODs desribed herein, as in the prior art. Instead, all amplification reactions for any one target nucleic acid are prepared from the same bulk solution or solutions, in one embodiment, from a first solution and a second solution. The combined reaction solution comprises all amplification reagents necessary, with the exception of the oligonucleotides. Oligonucleotides may then be optimized for optimal performance in the reaction solution. Optimization may include design of the oligonucleotide sequence, modifications to improve performance of oligonucleotides, and/or optimization of the concentration of oligonucleotides to obtain a good performance in the generic reaction solution. Optimization, thus, involves methods well known to the skilled person. However, solutions may also be prepared comprising already optimized oligonucleotide concentrations.

As shown in FIG. 5, in one aspect of the present invention, the kit (1021) comprises at least a first container (1022) comprising a first solution and a second container (1023) comprising a second solution. The kit may also comprise additional containers comprising additional solutions. These solutions are concentrated stock solutions which, when mixed with solutions comprising oligonucleotides and the target nucleic acid, comprise all reagents necessary for amplifying the target nucleic acid.

One aspect of the invention also relates to stock solutions comprising at least a first solution and a second solution, wherein the final concentration obtained by mixing the first and second solution is suitable for amplifying any one target nucleic acid, with an LOD as disclosed herein.

In one embodiment, the first and second solutions are used for preparing reaction mixtures for separately detecting different target nucleic acids in separate reaction vessels by adding oligonucleotides specific for the respective target nucleic acids.

In one embodiment, the first solution comprises Mn2+, in the presence or in the absence of Mg2+. In another embodiment, the first solution comprises Mn2+, in the absence of Mg2+. In still another embodiment, the first solution consists of MnOAc and non-active supplementary ingredients. Non-active supplementary ingredients are understood to be ingredients which are not necessary for test performance. Such ingredients are e.g. ingredients which act as a preservative. One non-active supplementary ingredient is NaN3. In this embodiment, $Mg^{2+}$ ions are absent. The final concentration is from 1, or from 2, or from 3 to 5, or to 4, or to 3.5 mM Mn2+. In one embodiment, Mn2+ is in the form of MnOAc.

In one embodiment, the stock solutions comprise a second solution comprising Tricine. For a 3⅓× concentrated second solution, concentrations of Tricine are from 100 mM, or from 150 mM to 300 mM, or to 250 mM. In one embodiment, said concentration is 200 mM. For stock solutions which are more concentrated or less concentrated, the concentrations of the 3⅓× concentrated stock solution are adapted accordingly. In another embodiment, the second solution does not comprise Tris.

In one embodiment, said stock solution further comprises potassium ions. Concentrations of a 3⅓× concentrated stock solution are from 300 mM, or from 350 mM to 500 mM, or to 450 mM. In another embodiment, concentration of potassium ions are 400 mM. For stock solutions which are more concentrated or less concentrated, the concentrations of the 3⅓× concentrated stock solution are adapted accordingly. In one embodiment, potassium acetate is used to provide potassium ions.

In one embodiment, the second solution additionally comprises glycerol. Concentrations of a 3⅓× concentrated stock solution are from 2%, or from 5%, or from 7% to 20%, or to 17%, or to 15%, or to 12%. In one embodiment, said glycerol concentration is 10%. For stock solutions which are more concentrated or less concentrated, the concentrations of the 3⅓× concentrated stock solution are adapted accordingly.

In one embodiment, the second solution additionally comprises DMSO. Concentrations of a 3⅓× concentrated stock solution are from 5%, or from 10%, or from 12%, or from 17% to 30%, or to 25%, or to 20%. In one embodiment, said concentration is 18%. For stock solutions which are more concentrated or less concentrated, the concentrations of the 3⅓× concentrated stock solution are adapted accordingly.

In one embodiment, the second solution additionally comprises a surfactant. In one embodiment, said surfactant is Tween, or Tween 20. Concentrations of a 3⅓× concentrated stock solution are from 0.01%, or from 0.025% to 0.1%, or to 0.075%. In another embodiment, the concentration is 0.05%. For stock solutions which are more concentrated or less concentrated, the concentrations of the 3⅓× concentrated stock solution are adapted accordingly.

The second solution may also comprise NaN3 at a concentration suitable for preservation of the solution. Concentrations of a 3⅓× concentrated stock solution are from 0.01%, or from 0.025% to 0.1%, or to 0.075%. In one embodiment, the concentration is 0.09%. For stock solutions which are more concentrated or less concentrated, the concentrations of the 3⅓× concentrated stock solution are adapted accordingly.

In one embodiment, the second solution further comprises an aptamer. Concentrations of a 3⅓× concentrated stock solution are from 0.1 uM, or from 0.25 uM, or from 0.5 uM to 1 uM, or to 0.8 uM, or to 0.75 uM. In one embodiment, concentration is 0.74 uM. For stock solutions which are more concentrated or less concentrated, the concentrations of the 3⅓× concentrated stock solution are adapted accordingly.

In one embodiment, the pH of a 3⅓× concentrated second solution is from 7.0, or from 7.5, or from 8.0 to 9.0, or to 8.5, or to 8.2. In one embodiment, the pH is 8.1. For stock solutions which are more concentrated or less concentrated, the pH is adapted accordingly.

In one aspect of the invention, the second solution comprises nucleotides necessary for amplification. In one embodiment, said nucleotides are deoxynucleotides (dNTP). In one embodiment, said nucleotides comprise dATP, dGTP, dCTP and dTTP or dUTP, or dATP, dGTP, dCTP and dUTP. Concentrations in a 3⅓× stock solution are from 5 mM, or from 4 mM, or from 3 mM to 0.5 mM, or to 1 mM, or to 2 mM. In one embodiment, the concentration, for dATP, dGTP and dCTP, is 1333.33 uM and for dUTP 2666.67 uM. For stock solutions which are more concentrated or less concentrated, the concentrations of the 3⅓× concentrated stock solution are adapted accordingly.

In one aspect of the present invention, the second solution additionally comprises a polymerase for amplification of nucleic acids. Embodiments of polymerases are disclosed herein. Concentrations of a 3⅓× concentrated stock solution are from 1000 KU/l, or from 2000 KU/l or from 2500 KU/l to 6000 KU/l, or to 5000 KU/l, or to 4000 KU/l. One concentration is 3000 KU/l. For stock solutions which are more concentrated or less concentrated, the concentrations of the 3⅓× concentrated stock solution are adapted accordingly.

In one aspect of the invention, the second solution additionally comprises UNG. Concentrations of a 3⅓× concentrated stock solution are from 450 KU/l, or from 500 KU/l, or from 600 KU/l to 1000 KU/l, or to 800 KU/l, or to 700 KU/l. One concentration is 670 KU/l UNG. For stock solutions which are more concentrated or less concentrated, the concentrations of the 3⅓× concentrated stock solution are adapted accordingly.

In one aspect of the invention, the second solution additionally comprises EDTA. The advantage of comprising EDTA is that before combining the first and second solution, the EDTA promotes an inactive state of the enzyme comprised in the second solution by complexing and inactivating contaminations that may promote enzyme activity. Concentrations of EDTA are from 1 uM, or from 10 uM, or from 40 uM to 200 uM, or to 100 uM, or to 50 uM, or 44 uM.

Stock solutions may be from 2×, or from 3×, or from 4× to 20×, or to 10×, or to 5× concentrated. In one embodiment, the stock solutions are 3⅓× or 5× concentrated. The x-fold concentration of different stock solutions may also be different.

The second solution may also be split up into one or more additional stock solutions. However, the stock solutions must provide concentrations of ingredients as described hereinbefore.

In one embodiment, the combination of the first and second solutions and optional additional solutions consists of manganese 2+, Tricine, potassium ions, glycerol, DMSO, Tween, sodium azide, dNTPs, polymerase, UNG and aptamer. Thus, no other ingredient is present in any one of the stock solutions.

The following salt concentrations are present in one embodiment of the final PCR reaction mixtures following combination of different stock solutions and, optionally, oligonucleotides:

Mn2+ has a final concentration from 1 mM, or from 2 mM, or from 2.5 mM to 5 mM, or to 4 mM, or to 3.5 mM. One final concentration is 3.3 mM.

Glycerol has final concentration from 1%, or from 2%, or from 2.5% to 5%, or to 4.5%, or to 4% or 3.5%. One concentration of glycerol is 3%. % is understood as % (v/v).

Tricine has a final concentration from 30 mM, or from 40 mM, or from 45 mM or 50 mM to 70 mM, or to 65 mM, or to 60 mM. One concentration is 60 mM Tricine.

DMSO has a final concentration from 0%, or from 1%, or from 2% or 3% to 6.5%, or to 6%, or to 5.5%. One embodiment is a DMSO final concentration of 5.4%. % is understood as % (v/v).

K+ has a final concentration from 80 mM, or from 90 mM, or from 100 mM or 110 mM to 150 mM, or to 145 mM, or to 135 mM or 125 mM. One K+ final concentration is 120 mM. One embodiment is a final concentration of 120 mM KOAc.

If Tween 20 is chosen to be comprised in a solution, the final concentration is from 0%, or from 0.005%, or from 0.015% to 0.03%, or to 0.025%, or to 0.02%. One Tween 20 concentration is 0.015%. % is understood as % (v/v).

The content of UNG in the reaction mixture is from 2 U, or from 5 U, or from 7 U or 8 U to 20 U, or to 15 U, or to 12 U per reaction. In one embodiment, 10 U per reaction of UNG are comprised. In one embodiment, the volume of the reaction mixture is 50 ul. Further concentrations can be calculated therefrom.

The content of polymerase, in one embodiment of Z05D in the final reaction, is from 25 U, or from 30 U, or from 35 U or 40 U to 55 U, or to 50 U, or to 45 U per reaction. In one embodiment, the content is 45 U per reaction. The volume of one embodiment of the reaction mixture is 50 ul. Further concentrations can be calculated therefrom.

The final reaction solution may further comprise non-active ingredients which are, e.g. suitable for preservation of the stock solutions and are, thus, also present in the final reaction mixture. Such non-active ingredients are, e.g., NaN3.

The present invention also relates to a stock solution as described herein, additionally comprising oligonucleotides. Concentrations in a 3⅓× stock solution of oligonucleotides are from 0.1 uM, or from 0.2667 uM to 5 uM, or to 4 uM. In one aspect, the second solution comprises optimized concentrations of oligonucleotides for amplification of the target and control nucleic acids. In another aspect, the second solution comprises 0.1 uM to 4 uM of any one oligonucleotide for amplifying and detecting the target nucleic acids. In one embodiment, the oligonucleotide concentration is between 0.05 uM and 0.5 uM, or 0.3 uM. In one embodiment, the concentration used of any one oligonucleotide is identical. Thus, in a embodiment, 0.3 uM of any one oligonucleotide is used. In other embodiments, concentrations of oligonucleotides are individually optimized and are in a range between 0.025 uM and 0.75 uM or 0.05 uM and 0.5 uM. If the second solution additionally comprises oligonucleotides, additional ingredients may be introduced into the solution at low concentrations, such as Tris at concentration of below 1 mM, or of below 0.5 mM, or of equal or less than 0.3 mM. EDTA may be introduced at concentrations of less than 5 uM, or less than 2.5 uM, or 1 y less than 1 uM. If Tricine or potassium ions are introduced with the oligonucleotides, the concentration of the second solution may initially vary by 10% to 15%, or the final stock solution including oligonucleotides may vary by 10% to 15% of the concentrations herein described. The skilled person will know how to optimize the concentration of each oligonucleotide to be used in the solutions of the present invention.

In one aspect of the present invention, the second solution additionally comprises oligonucleotides to detect an internal control nucleic acid. Embodiments of control nucleic acids and oligonucleotides are disclosed herein. The concentrations of said oligonucleotides to detect an internal control are optimized as described hereinbefore. Concentrations are as disclosed hereinbefore. In one embodiment, said second solution comprises oligonucleotides to detect internal control nucleic acids in the absence of oligonucleotides for detecting the target nucleic acids.

In one embodiment of the kit hereinbefore described, the kit additionally comprises at least one container containing a control nucleic acid. Embodiments of said control nucleic acids are disclosed herein. In one embodiment, said kit comprises one container with a control nucleic acid comprising DNA, and a further container comprising a control nucleic acid comprising RNA. This kit is of particular use for simultaneous testing of both RNA and DNA target nucleic acids.

In one aspect of the system hereinbefore described, the concentrations of said amplification reagents are identical in all reaction vessels. Identical is meant to include a variability of 20%, or 15%, or 10%.

A "separation station" is a device or a component of an analytical system allowing for the isolation of the solid support material from the other material present in the fluid sample. Such a separation station can e.g. comprise, but is not limited to, a centrifuge, a rack with filter tubes, a magnet, or other suitable components. In one embodiment of the invention, the separation station comprises one or more magnets. In one embodiment, one or more magnets are used for the separation of magnetic particles, e.g. magnetic glass particles, as a solid support. If, for example, the fluid sample and the solid support material are combined together in the wells of a multiwell plate, then one or more magnets comprised by the separation station can e.g. be contacted with the fluid sample itself by introducing the magnets into the wells, or said one or more magnets can be brought close to the outer walls of the wells in order to attract the magnetic particles and subsequently separate them from the surrounding liquid.

Useful in the context of the present invention and the separation station is further a method of isolating and purifying a nucleic acid. The method comprises the steps of binding a nucleic acid to magnetic particles in a vessel of a multiwell plate. The vessel comprises an upper opening, a central part and a bottom part. The bound material is then separated from unbound material contained in a liquid when the major part of the liquid is located above the section where the conical part of the vessel is replaced by the central part with the rectangular shape, by moving a magnet from a second position to a first position and, in said first position, applying a magnetic field to the central part and, optionally, additionally applying a magnetic field to the bottom part of said vessel. The magnetic particles can optionally be washed with a washing solution. A small volume of liquid, wherein the major part of the liquid is located below the section where the conical part of the vessel is replaced by the central part with the rectangular shape is separated from said magnetic particles by selectively applying a magnetic field to the bottom part of said vessel.

An "amplification station" (403) comprises a temperature-controlled incubator for incubating the contents of at least two reaction vessels. It further comprises a variety of reaction vessels like tubes or plates, in which a reaction for the analysis of the sample such as PCR takes place. The outer limits or walls of such vessels are chemically inert such that they do not interfere with the amplification reaction taking place within. For the ease of handling and to facilitate automation, the at least two reaction vessels are in an integral arrangement, so they can be manipulated together.

Consequently, one aspect of the invention is the analytical system described above, wherein the at least two reaction vessels are combined in an integral arrangement. Integral arrangements can e.g. be vials or tubes reversibly or irreversibly attached to each other or arranged in a rack. In one embodiment, the integral arrangement is a multiwell plate.

In one aspect of the present invention, the system additionally comprises a multiwell plate for amplifying said target nucleic acids.

In one aspect of the present invention, the system additionally comprises a multiwell plate for isolating said target nucleic acids.

In one embodiment, at least two reaction vessels combined in an integral arrangement are transported between stations of the system.

In a second embodiment, the purified target nucleic acid is transferred from the separation station to the amplification station. In one embodiment, a pipettor comprising pipets with attached pipet tips transfers the liquid comprising the purified nucleic acid.

In a third embodiment, the purified nucleic acid is transferred from the separation station to a reaction vessel in an integral arrangement held in a holding station. In one embodiment the reaction vessel in an integral arrangement is then transferred from the holding station to the amplification station.

The analytical system according to the invention, in one embodiment, further comprises a pipetting unit. Said pipetting unit comprises at least one pipet, or multiple pipets. In one embodiment, the multiple pipets are combined in one or more integral arrangements, within which the pipets can be manipulated individually. Pipets used in the context of the invention are pipets comprising pipet tips as described herein. In another embodiment, the pipets are pipetting needles.

Alternatively, a reaction vessel or arrangement of reaction vessels used for sample preparation in the separation station and containing the fluid comprising the purified target nucleic acids may be transferred from the separation station to the amplification station.

For this purpose, in one embodiment, the analytical system according to the invention further comprises a transfer unit. In one embodiment the transfer unit additionally comprises a robotic device. In one aspect, the device additionally comprises a handler.

For the reasons set out above in the context of the process according to the invention, the following are further aspects of the invention:

The analytical system (440) described above wherein at least one reaction vessel comprises an RNA target nucleic acid and a DNA target nucleic acid.

The analytical system (440) described above, wherein at least one reaction vessel comprises an RNA target nucleic acid, and at least one other reaction vessel comprises a DNA target nucleic acid.

In one aspect, the analytical system (440) described above further comprises one or more elements selected from the group consisting of:
  a detection module (403) for detecting signals evoked by an analyte
  a sealer (410)
  a storage module (1008) for reagents and/or disposables.
  a control unit (1006) for controlling system components.

Exemplary systems are shown in FIGS. 3 and 4. A "detection module" (403) can e.g. be an optical detection unit for detecting the result or the effect of the amplification procedure. An optical detection unit may comprise a light source, e.g. a xenon lamp, optics such as mirrors, lenses, optical filters, fiber optics for guiding and filtering the light, one or more reference channels, or a CCD camera or a different camera.

A "sealer" (410) is constructed and arranged to seal any vessels used in connection with the analytical system according to the invention. Such a sealer can, for example, seal tubes with appropriate caps, or multiwell plates with foil, or other suitable sealing materials.

A "storage module" (1008) stores the necessary reagents to bring about a chemical or biological reaction important for analysis of the fluid sample. It can also comprise further components useful for the method of the invention, e.g. disposables such as pipet tips or vessels to be used as reaction vessels within the separation station and/or the amplification station.

In one aspect, the analytical system according to the invention further comprises a control unit for controlling system components (FIG. 4). Such a "control unit" (1006) may comprise software for ensuring that the different components of said analytical system work and interact correctly and with the correct timing, e.g. moving and manipulating components such as pipets in a coordinated manner. The control unit may also comprise a processor running a real-time operating system (RTOS), which is a multi-tasking operating system intended for real-time applications. In other words the system processor is capable of managing real-time constraints, i.e. operational deadlines from event to system response regardless of system load. It controls in real time that different units within the system operate and respond correctly according to given instructions.

The exemplary system shown in FIG. 3 displays the following features: it comprises an analyzer (400) with a module for preparing samples (402), a module for processing samples (401), a module for amplification (403) and a transfer module (404). It additionally comprises a liquid handling module (500). The module for preparing samples (402) comprises a holding station (470). The module for processing samples (401) comprises a holding station (470), a processing or separation station (201, 230), a holding station (330), a heating device (128) and a sealing station (128). The module for amplification (403) comprises an incubator (405). The analyzer (400) additionally comprises an air lock (460) between module (401) and module (403). Some of these features are also displayed in the exemplary system shown in FIG. 4. In FIG. 4, the module for preparing samples (402) further comprises a holder (1007) for holding a tip rack (70) which holds pipette tips (3,4). It further comprises a holder (1007) for holding a deep well plate (101), which comprises receptacles (103) to which liquid samples (1011) can be added. It also comprises a holder (1003) for a rack (1002) comprising first receptacles (1001) which comprise liquid samples (1010). The module for preparing samples (402) further comprises a first pipetting device (700) which is controlled by a first processor (1004). The module for processing samples (401) comprises separation station (201) or heating device (128) which comprises processing plate (101). Processing plate (101) comprises receptacles (103). It also comprises holding station (470) which holds pipette tip rack (470) comprising pipette tips (3,4). The module for processing samples (401) further comprises pipetting device (35) which is controlled by second processor (1005). The analytical system (440) comprises analyzer (400) and control unit (1006), which controls first processor (1004) and second processor (1005). Furthermore, the analyzer (400) comprises transfer system (480).

In one aspect the present invention relates to a kit for separately amplifying at least two target nucleic acids, the kit comprising at least one container, wherein the container comprises a solution for use in separately amplifying any one of at least two different target nucleic acids.

A container (1022, 1023, 1024) is any type of storage vessel for holding liquids.

In one embodiment, the kit comprises at least two containers, wherein a first container comprises a first solution, and a second container comprises a second solution for preparing a combined solution for use in separately amplifying any one of at least two target nucleic acids.

In one embodiment, the first solution comprises at least one salt necessary for amplifying nucleic acids, and the second solution comprises at least an enzyme for amplifying nucleic acids and dNTPs.

The present invention also relates to a kit (1021) comprising a first container (1022) and a second container (1023), the first container comprising a solution of $Mn^{2+}$ ions, or MnAc, and the second container comprising an enzyme for amplifying nucleic acids. In one aspect, the second container additionally comprises dNTPs.

Further embodiments for the solutions are as hereinbefore described.

In a further aspect, the present invention relates to a method for amplifying at least one target nucleic acid that may be present in at least one fluid sample, comprising providing at least one container comprising a solution for amplifying the target nucleic acid, adding oligonucleotides specific for amplifying the target nucleic acid to the solution, combining the target nucleic acid with the solution and the oligonucleotides, incubating the target nucleic acid, the solution and the oligonuleotides in a reaction vessel for a period of time and under conditions sufficient for an amplification reaction indicative of the presence or absence of the target nucleic acid to occur.

In one aspect, a first container comprises a first solution comprising at least one salt necessary for amplifying a nucleic acid, and wherein a second container comprises a second solution comprising an enzyme and deoxynucleotides necessary for amplifying a nucleic acid, wherein the first and the second solution are combined in the reaction vessel to obtain the solution.

An embodiment of the system and method according to the present invention is shown in FIG. 6. A first and/or second solution (1028, 1029) comprised in container (1022) and/or (1023) comprises all reagents necessary for amplification, with the exception of oligonucleotides. The solution (1028) and/or (1029) is combined with a solution of oligonucleotides (1025), which is contained in container (1024). The solutions are combined in container (1026), thus constituting solution (1027). Solution (1027) is then transferred to container (1030). This container is designed for loading into analyzer (400). In the present method, the container (1030) is loaded into analyzer (400).

Further embodiments of the solutions are as described hereinbefore.

The present invention is now exemplified with the following non-limiting examples:

EXAMPLES

The instruments listed in the following table were used according to the instructions of the respective manufacturer:

| Instrument | Manufacturer |
| --- | --- |
| Hamilton Star | Hamilton Medical AG (Bonaduz, CH) |
| Light Cycler 480 | Roche Diagnostics GmbH (Mannheim, DE) |
| Chameleon Sealer | K biosystems (Essex, UK) |
| Compressor | K biosystems (Essex, UK) |

Sample Preparation

This example describes a process for isolating and simultaneously amplifying at least a first and a second target nucleic acid using a single generic internal control nucleic acid.

In brief, in the depicted embodiment, realtime PCR is carried out simultaneously and under identical conditions on a panel of several different targets comprising bacteria (*Chlamydia trachomatis*, CT) as well as a DNA virus (HBV) and an RNA virus (HIV).

The following samples were prepared and subsequently analyzed:

| Reagent | Manufacturer: |
| --- | --- |
| HIV-1M Secondary Standard, 50'000 cp/ML | Roche |
| HBV Secondary Standard, 400 IU/ML | Roche |
| CT (DNA POS CTL pCHL-1) | Roche |

Suitable standards or other types of targets are available to the skilled artisan.

For sample preparation the following reagents were used as diluents:

| Reagent | Manufacturer: |
| --- | --- |
| K3 EDTA Plasma, PCR neg. | Roche |

The following dilutions were prepared in advance and stored over night (plasma dilutions at −60 to −90° C.):

| Target | Concentration | Matrix |
| --- | --- | --- |
| HBV | 50 IU/mL | K3 EDTA plasma |
| HIV-1M | 100 cp/mL | K3 EDTA plasma |

Each respective sample (500 ul) and each respective specimen diluent (350 ul) were pipetted manually into a deepwell plate, wherein each sample was added to three different wells for triplicate analysis. To each well containing an HIV or HBV sample, 50 ul of an internal control nucleic acid were manually added. For the qualitative HIV assay, an RNA serving as a qualitative control was added (100 armored particles/sample). For the quantitative HIV assay, an RNA serving as a quantitative standard was added (500 armored particles/sample). For the quantitative HBV assay, a DNA serving as a quantitative standard was added (1E4 copies/sample). The sequence of said control nucleic acids was identical in all cases and selected from the group of SEQ ID NOs 45-48.

Figure 1:
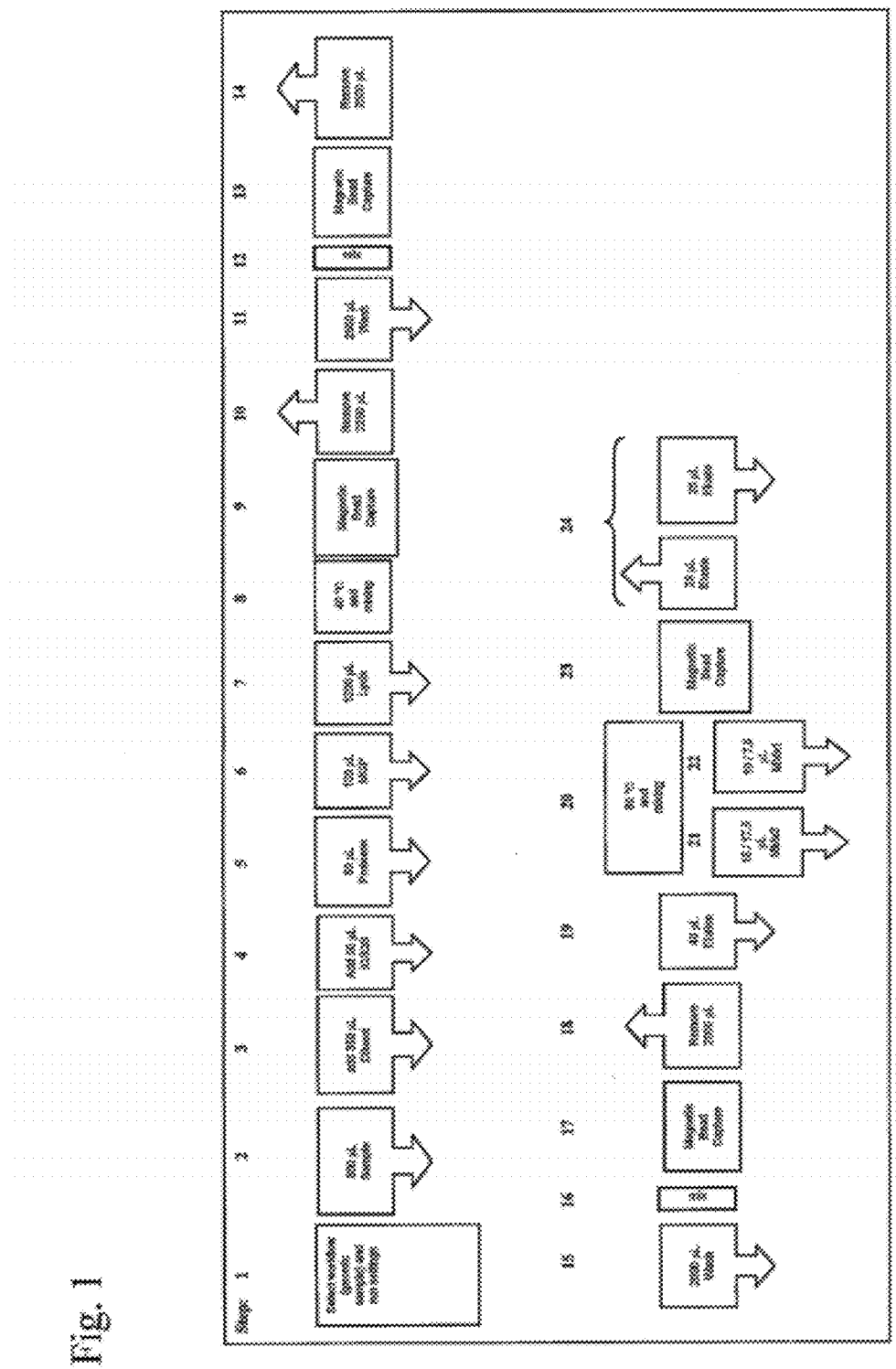
FIG. 1: Schematic depiction of the sample preparation workflow as used in an embodiment of the invention.
}

Sample preparation was performed on a Hamilton Star (Hamilton, Bonaduz, CH), following the workflow according to the scheme depicted in FIG. 1.

After the final step, the process head of the Hamilton Star apparatus added the respective mastermixes (MMxs) containing amplification reagents to each well, mixed the fluids containing the isolated nucleic acids with the MMx and transferred each resulting mixture to a corresponding well of a microwell plate in which the amplification was carried out.

Amplification and Detection

For amplification, two stock solutions R1 and R2 were prepared, either separately for separate target nucleic acids (R1-HBV and R2-HBV, R1-HCV and R2-HCV, R1-HIV and R2-HIV) or as generic solutions R1-HxV and R2-HxV of the following concentrations in a total volume of 50 ul:

R1-HBV: 2.5 mM MnOAc, pH 6.1, 2.5 mM MgOAc pH 6.1 and 0.02% Sodium azide pH 7.0.

R2-HBV: 0.03% Sodium azide pH 7.0, 25.2 mM KOH, 121.8 mM KOAc pH 7.0, 5% Glycerol, 0.03% Tween 20, 40 mM Tricine pH 7.7, 0.2325 uM aptamer, 2 U UNG, 0.42 mM dGTP, 0.42 mM dATP, 0.42 mM dCTP, 0.84 mM dUTP, 35U Z05D-polymerase, 1.2 uM HBV fwd primer (Seq ID 36), 0.1 uM HBV sense probe (Seq ID 38), 1.2 uM HBV rev primer (Seq ID 37); 0.6 uM Control fwd primer (Seq ID 42), 0.6 uM Control rev primer (Seq ID 43), 0.15 uM Control probe (Seq ID 44).

R1-HCV: 2.5 mM MnOAc, pH 6.1, and 0.02% Sodium azide pH 7.0.

R2-HCV: 0.03% Sodium azide pH 7.0, 4% DMSO, 110 mM KOAc pH 7.0, 4% Glycerol, 0.02% Igepal, 50 mM Tricine pH 8.0, 2.08% v/v of TRIS (10 mM), pH 8.0, 0.2222 uM aptamer, 10 U UNG, 0.5 mM dGTP, 0.5 mM dATP, 0.5 mM dCTP, 1.0 mM dUTP, 30U Z05D-polymerase, 2.25% v/v probe storage buffer JA270, 0.1 uM HCV fwd primer, 0.1 uM HCV rev primer, 0.1 uM HCV probe 1, 0.1 uM HCV probe 2; 0.3 uM control fwd primer, 0.3 uM control rev primer, 0.1 uM control probe.

R1-HIV: 3.5 mM MnOAc, pH 6.1, and 0.02% Sodium azide pH 7.0.

R2-HIV: 0.03% Sodium azide pH 7.0, 1% DMSO, 110 mM KOAc pH 7.0, 4.5% Glycerol, 45 mM Tricine pH 7.7, 60 mM Tris pH 7.7, 0.3 uM aptamer, 10 U UNG, 1.75 mM dGTP, 1.75 mM dATP, 1.75 mM dCTP, 1.75 mM dUTP, 40U Z05D-polymerase, 0.3 uM HIV-GAG fwd primer, 0.3 uM HIV-GAG rev primer, 0.1 uM HIV-GAG probe, 0.1 uM HIV-LTR fwd primer 1, 0.1 uM HIV-LTR fwd primer 2, 0.1 uM HIV-LTR rev primer 1, 0.1 uM HIV-LTR rev primer 2; 0.1 uM HIV-LTR probe, 0.3 uM control fwd primer, 0.3 uM control rev primer, 0.1 uM control probe.

R1-HxV: 3.3 mM MnOAc, pH 6.1, and 0.02% Sodium azide pH 7.0.

R2-HxV for HBV: 0.03% Sodium azide pH 7.0, 5.4% DMSO, 120 mM KOAc pH 7.0, 3% Glycerol, 0.02% Tween 20, 60 mM Tricine pH 8.0, 0.2222 uM aptamer, 10 U UNG, 0.4 mM dGTP, 0.4 mM dATP, 0.4 mM dCTP, 0.8 mM dUTP, 45 U Z05D polymerase, 1.2 uM HBV fwd primer, 0.1 uM MY sense probe, 1.2 uM HBV rev primer; 0.6 uM control fwd primer, 0.6 uM control rev primer, 0.15 uM control probe.

R2-HxV for HCV: 0.03% Sodium azide pH 7.0, 5.4% DMSO, 120 mM KOAc pH 7.0, 3% Glycerol, 0.02% Tween 20, 60 mM Tricine pH 8.0, 0.2222 uM aptamer, 10 U UNG, 0.4 mM dGTP, 0.4 mM dATP, 0.4 mM dCTP, 0.8 mM dUTP, 45 U Z05D polymerase, 0.1 uM HCV fwd primer, 0.1 uM HCV rev primer 1, 0.1 uM HCV rev primer 2, 0.1 uM HCV probe 1, 0.1 uM HCV probe 2; 0.3 uM control fwd primer, 0.3 uM control rev primer, 0.1 uM control probe.

R2-HxV for HIV: 0.03% Sodium azide pH 7.0, 5.4% DMSO, 120 mM KOAc pH 7.0, 3% Glycerol, 0.02% Tween 20, 60 mM Tricine pH 8.0, 0.2222 uM aptamer, 10 U UNG, 0.4 mM dGTP, 0.4 mM dATP, 0.4 mM dCTP, 0.8 mM dUTP, 45 U Z05D polymerase, 0.3 uM HIV-GAG fwd primer, 0.3 uM HIV-GAG rev primer, 0.1 uM HIV-GAG probe, 0.1 uM HIV-LTR fwd primer 1, 0.1 uM HIV-LTR fwd primer 2, 0.1 uM HIV-LTR rev primer 1, 0.1 uM HIV-LTR rev primer 2; 0.1 uM HIV-LTR probe, 0.3 uM control fwd primer, 0.3 uM control rev primer, 0.1 uM control probe.

The final concentrations of amplification reagents is shown in the following table:

TABLE 1

| | | HBV v3.0A | HCV v6.0.1 | HIV v4.2 | HBV HxV | HCV HxV | HIV HxV |
|---|---|---|---|---|---|---|---|
| R1 | Water | | | | | | |
| | MnOAc (100 mM), pH 6.1 | 2.5 mM | 2.5 mM | 3.5 mM | | 3.3 mM | |
| | MgOAC (100 mM), pH 6.1 | 2.5 mM | | | | | |
| | Sodium Acid (10%), pH. 7.0 | | | 0.02% | | | |
| R2 | DMSO (80%) | | 4% | 1% | | 5.40% | |
| | Sodium Acid (10%), pH 7.0 | | | 0.03% | | | |
| | KOH (4 mM) | 25.2 mM | | | | | |
| | KOAc (2 mM), pH 7.0 | 121.8 mM | 110 mM | 110 mM | | 120 mM | |
| | Glycerol (80% v/v) | 5% | 4% | 4.50% | | 3% | |
| | Tween 20 (80%) | 0.03% | | | | | |
| | Tween 20 (50%) | | | | | 0.02% | |
| | Igepal (8%) | | 0.02% | | | | |
| | Tricine (1M), pH 7.7 | 40 mM | | 45 mM | | | |
| | Tricine (1M), pH 8.0 | | 50 mM | | | 60 mM | |
| | Tris (4M), pH 7.7 | | | 60 mM | | | |
| | Tris (10 mM), pH 8.0 | | 2.08% v/v | | 3.58% v/V | 3% v/v | 1.25% v/v |
| | NTQ21-46A-Aptamer | 0.2325 µM | 0.2222 µM | 0.3 µM | | 0.2222 µM | |
| | UNG (50 U/uL) | 2 U | 10 U | 10 U | | 10 U | |
| | dGTP (100 µM) | 0.42 mM | 0.5 mM | 1.75 mM | | 0.4 mM | |
| | dATP (100 µM) | 0.42 mM | 0.5 mM | | | 0.4 mM | |
| | dCTP (100 µM) | 0.42 mM | 0.5 mM | | | 0.4 mM | |
| | dUTP (100 µM) | 0.84 mM | 1 mM | | | 0.8 mM | |
| | ZO5-D Polymerase (200 U/ul) | 35 U | 30 U | 40 U | | 45 U | |
| | Probe Storage Buffer HEX/FAM/CY5.5, pH 8.2 | | | | 0.66% v/v | 0.92% v/v | 0.25% v/v |
| | Probe Storage Buffer JA270 | | 2.25% v/v | | 1.33% v/v | | 1.33% v/V |
| | Water | | | | | | | concentrations in 50 µl

Oligonucleotide sequences are selected from Seq ID No. 1 to 16 for HIV-1-GAG forward or reverse primers, and 17 to 21 for HIV-1-GAG probe, Seq ID No. 22 to 29 for HIV-1-LTR forward or reverse primers, Seq ID No. 33 or 34 for HIV-1-LTR probe, Seq ID No. 30 to 32 for HIV-2 forward or reverse primers, Seq ID 35 for HIV-2 probe, Seq ID No. 36 to 37 for HBV forward and reverse primers, Seq ID No. 38 for HBV probe, Seq ID No. 42 to 44 for internal control, Seq ID No. 49 to 63 for HCV forward, Seq ID No. 64 to 92 for reverse primers or probes.

For amplification and detection, the microwell plate was sealed with an automated plate sealer (see above), and the plate was transferred to a LightCycler 480 (see above).

The following PCR profile was used:

TABLE 2

Thermo cycling profile

| Program Name | Target (° C.) | Acquisition Mode | Hold (hh:mm:ss) | Ramp Rate (° C./s) | Cycles | Analysis Mode |
|---|---|---|---|---|---|---|
| Pre-PCR | 50 | None | 00:02:00 | 4.4 | 1 | None |
|  | 94 | None | 00:00:05 | 4.4 |  |  |
|  | 55 | None | 00:02:00 | 2.2 |  |  |
|  | 60 | None | 00:06:00 | 4.4 |  |  |
|  | 65 | None | 00:04:00 | 4.4 |  |  |
| 1st Measurement | 95 | None | 00:00:05 | 4.4 | 5 | Quantification |
|  | 55 | Single | 00:00:30 | 2.2 |  |  |
| 2nd Measurment | 91 | None | 00:00:05 | 4.4 | 45 | Quantification |
|  | 58 | Single | 00:00:25 | 2.2 |  |  |
| Cooling | 40 | None | 00:02:00 | 2.2 | 1 | None |

Detection Format (Manual)

| Filter Combination | Integration Time (sec) |
|---|---|
| 435-470 | 1 |
| 495-525 | 0.5 |
| 540-580 | 0.5 |
| 610-645 | 0.5 |
| 680-700 | 1 |

The Pre-PCR program comprises initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription.

PCR cycling is divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

Using this profile on all samples comprised on the microwell plate mentioned above, amplification and detection was achieved in all samples, as depicted in FIG. 2. This shows that the sample preparation prior to amplification was also successfully carried out.

The results for the qualitative and quantitative HIV internal controls and the quantitative HBV internal control are depicted separately in FIG. 2 for the sake of clarity. It can be seen that the controls were also successfully amplified in all cases. The quantitation of the HIV and HBV targets in the quantitative setup were calculated by comparison with the internal control nucleic acid serving as a quantitative standard.

Comparative results are shown below:

TABLE 3

LOD studies:

| | | MMx Year End 2009 | | | MMx HxV Assessment | | |
|---|---|---|---|---|---|---|---|
| Assay | Matrix | Probit | CI | >95% Hitrate | Probit | CI | >95% Hitrate |
| HBV | Plasma | 2.11 IU/mL | 1.5-3.8 | 3 IU/mL | 1.85 IU/mL | 1.3-3.8 | 1.5 IU/mL |
|  | Serum | 1.37 IU/mL | 1.0-3.2 | 1.5 IU/mL | 2.45 IU/mL | 1.7-4.6 | 3 IU/mL |
| HCV | Plasma | 7.94 IU/mL | 6.0-12.4 | 15 IU/mL | 5.92 IU/mL | 4.3-10.6 | 7.5 IU/mL |
|  | Serum | 28.18 IU/mL | 15.6-112.8 | 15 IU/mL | 5.97 IU/mL | no CI | 3 IU/mL |
| HIV | Plasma | 15.14 cp/mL | 10.9-25.3 | 20 cp/mL | 16.8 cp/mL | 11.9-29.1 | 20 cp/mL |

TABLE 4

Inclusivity:

| Sample | Genotype | Concentration | hit/# replicates HIV v4.2 | hitrate HIV v4.2 | hit/# replicates HIV HxV | hitrate HIV HxV |
|---|---|---|---|---|---|---|
| BBI #1 | A | 20 cp/mL | 9/12 | 75.00% | 9/12 | 75.00% |
| BBI #4 | CRF02_AG | (PRD LOD) | 9/12 | 75.00% | 12/12 | 100.00% |
| BBI #5 | B |  | 11/12 | 91.66% | 12/12 | 100.00% |

TABLE 4-continued

Inclusivity:

| Sample | Genotype | Concentration | hit/# replicates HIV v4.2 | hitrate HIV v4.2 | hit/# replicates HIV HxV | hitrate HIV HxV |
|---|---|---|---|---|---|---|
| BBI #8 | C | | 12/12 | 100.00% | 10/12 | 83.33% |
| BBI #9 | D | | 12/12 | 100.00% | 12/12 | 100.00% |
| BBI #12 | CRF01_AE | | 7/12 | 58.33% | 12/12 | 100.00% |
| BBI #14 | F | | 11/12 | 91.66% | 12/12 | 100.00% |
| BBI #15 | G | | 11/12 | 91.66% | 11/12 | 91.60% |
| BBI #17 | H | | 12/12 | 100.00% | 9/12 | 75.00% |
| BBI 03 | HIV-1O | | 12/12 | 100.00% | 12/12 | 100.00% |
| BBI 04 | HIV-1O | | 12/12 | 100.00% | 12/12 | 100.00% |
| ARP190 YBF 30 | HIV-1N | | 12/12 | 100.00% | 12/12 | 100.00% |
| BBI #1 | A | 30 cp/mL | 10/12 | 83.33% | 12/12 | 100.00% |
| BBI #4 | CRF02_AG | | 11/12 | 91.66% | 12/12 | 100.00% |
| BBI #5 | B | | 12/12 | 100.00% | 12/12 | 100.00% |
| BBI #8 | C | | 11/12 | 91.66% | 11/12 | 91.66% |
| BBI #9 | D | | 12/12 | 100.00% | 12/12 | 100.00% |
| BBI #12 | CRF01_AE | | 11/12 | 91.66% | 12/12 | 100.00% |
| BBI #14 | F | | 12/12 | 100.00% | 12/12 | 100.00% |
| BBI #15 | G | | 12/12 | 100.00% | 12/12 | 100.00% |
| BBI #17 | H | | 12/12 | 100.00% | 11/12 | 91.66% |
| BBI 03 | HIV-1O | | — | — | — | — |
| BBI 04 | HIV-1O | | — | — | — | — |
| ARP190 YBF 30 | HIV-1N | | 12/12 | 100.00% | 12/12 | 100.00% |

TABLE 5

| Sample | Genotype | Concentration | hit/# replicates HIV v4.2 | hitrate HIV v4.2 | hit/# replicates HIV HxV | hitrate HIV HxV |
|---|---|---|---|---|---|---|
| BBI #1 | A | 20 cp/mL | 9/12 | 75.00% | 9/12 | 75.00% |
| BBI #4 | CRF02_AG | (PRD LOD) | 9/12 | 75.00% | 12/12 | 100.00% |
| BBI #5 | B | | 11/12 | 91.66% | 12/12 | 100.00% |
| BBI #8 | C | | 12/12 | 100.00% | 10/12 | 83.33% |
| BBI #9 | D | | 12/12 | 100.00% | 12/12 | 100.00% |
| BBI #12 | CRF01_AE | | 7/12 | 58.33% | 12/12 | 100.00% |
| BBI #14 | F | | 11/12 | 91.66% | 12/12 | 100.00% |
| BBI #15 | G | | 11/12 | 91.66% | 11/12 | 91.60% |
| BBI #17 | H | | 12/12 | 100.00% | 9/12 | 75.00% |
| BBI 03 | HIV-1O | | 12/12 | 100.00% | 12/12 | 100.00% |
| BBI 04 | HIV-1O | | 12/12 | 100.00% | 12/12 | 100.00% |
| ARP190 YBF 30 | HIV-1N | | 12/12 | 100.00% | 12/12 | 100.00% |
| BBI #1 | A | 30 cp/mL | 10/12 | 83.33% | 12/12 | 100.00% |
| BBI #4 | CRF02_AG | | 11/12 | 91.66% | 12/12 | 100.00% |
| BBI #5 | B | | 12/12 | 100.00% | 12/12 | 100.00% |
| BBI #8 | C | | 11/12 | 91.66% | 11/12 | 91.66% |
| BBI #9 | D | | 12/12 | 100.00% | 12/12 | 100.00% |
| BBI #12 | CRF01_AE | | 11/12 | 91.66% | 12/12 | 100.00% |
| BBI #14 | F | | 12/12 | 100.00% | 12/12 | 100.00% |
| BBI #15 | G | | 12/12 | 100.00% | 12/12 | 100.00% |
| BBI #17 | H | | 12/12 | 100.00% | 11/12 | 91.66% |
| BBI 03 | HIV-1O | | — | — | — | — |
| BBI 04 | HIV-1O | | — | — | — | — |
| ARP190 YBF 30 | HIV-1N | | 12/12 | 100.00% | 12/12 | 100.00% |

TABLE 6

| Sample | Genotype | Concentration | hit/# replicates HBV RL5 | hitrate HBV RL5 | hit/# replicates HBV HxV | hitrate HBV HxV |
|---|---|---|---|---|---|---|
| BBI02 | A | 10 IU/mL | 12/12 | 100% | 12/12 | 100% |
| T#5 | B | | 12/12 | 100% | 12/12 | 100% |
| T#11 | C | | 12/12 | 100% | 12/12 | 100% |
| T#102256 | D | | 12/12 | 100% | 6/6* | 100% |
| BBI08 | E | | 12/12 | 100% | 12/12 | 100% |
| T#101235 | F | | 12/12 | 100% | 6/6* | 100% |

TABLE 6-continued

| Sample | Genotype | Concentration | hit/# replicates HBV RL5 | hitrate HBV RL5 | hit/# replicates HBV HxV | hitrate HBV HxV |
|---|---|---|---|---|---|---|
| T#12 | G | | 12/12 | 100% | 6/6* | 100% |
| PIT 1896 | Pre-Core | | 11/12 | 91.60% | 6/6* | 100% |
| BBI02 | A | 30 IU/mL | 12/12 | 100% | 12/12 | 100% |
| T#5 | B | | 12/12 | 100% | 12/12 | 100% |
| T#11 | C | | 12/12 | 100% | 12/12 | 100% |
| T#102256 | D | | 12/12 | 100% | 6/6* | 100% |
| BBI08 | E | | 12/12 | 100% | 12/12 | 100% |
| T#101235 | F | | 12/12 | 100% | 6/6* | 100% |
| T#12 | G | | 12/12 | 100% | 6/6* | 100% |
| PIT 1896 | Pre-Core | | 12/12 | 100% | 6/6* | 100% |

Table 7 shows an additional example of final concentrations obtained from stocks of a second solution for use in the method of the present invention in a PCR reaction of 50 ul:

TABLE 7

| Glycerol (%, w/v) | 3.00% |
|---|---|
| Tricine | 60.00 mM |
| DMSO (%, v/v) | 5.40% |
| KOH | na |
| KOAc | 120.00 mM |
| Tween 20 | 0.015 |
| EDTA | 43.9 µM |
| control fwd primer | 0.150 µM |
| control rev primer | 0.150 µM |
| control probe | 0.100 µM |
| NTQ21-46 A | 0.222 µM |
| ZO5D | 0.9 U/µL (45 U/rxn) |
| UNG | 0.2 U/µL (10 U/rxn) |
| Sodium Acid | 0.027 |

The invention claimed is:

1. An automated process for amplifying and determining the quantity of at least a first and a second target nucleic acid that may be present in at least one fluid sample, said process comprising the steps of:

a) separately incubating in at least two reaction vessels said target nucleic acids with a solution comprising amplification reagents, and oligonucleotides specific for said first or second target nucleic acid, wherein said amplification reagents comprise a polymerase with reverse transcriptase activity, for a period of time and under conditions suitable for transcription of RNA by said polymerase with reverse transcriptase activity to occur, b) separately incubating in said at least two reaction vessels said target nucleic acids with said solution comprising amplification reagents, and oligonucleotides specific for said first or second target nucleic acid for a period of time and under conditions sufficient for an amplification reaction of said first and second target nucleic acid to occur, and c) determining the quantity of said first and second target nucleic acid by referencing to an external calibration or by implementing an internal quantitative standard;

wherein said solutions in said first and in said second reaction vessels comprise the same concentration of amplification reagents, and wherein oligonucleotides for said first target nucleic acid are present in the first of said at least two reaction vessels and absent in the second of said at least two reaction vessels, and oligonucleotides for said second target nucleic acid are present in the second of said at least two reaction vessels and absent in the first of said at least two reaction vessels, wherein said first target nucleic acid is an RNA target nucleic acid and said second target nucleic acid is a DNA target nucleic acid, and wherein the conditions for transcription in step a) and for amplification in step b) are identical for said at least first and second target nucleic acids comprised in said first and second reaction vessels.

2. The automated process of claim 1, wherein said process is preceded by the steps of:

providing a plurality of vessels comprising different types of fluid samples, combining together a solid support material and said plurality of different types of fluid samples in said plurality of vessels for a period of time and under conditions sufficient to permit nucleic acids comprising the target nucleic acids to be immobilized on the solid support material, isolating the solid support material from the other material present in the fluid samples in a separation station, and purifying the nucleic acids in a separation station by separating the fluid sample from the solid support material and washing the solid support material one or more times with a wash buffer, wherein the conditions and the period of time in said combining step are identical for the any one of the plurality of different types of fluid samples.

3. The process of claim 1 wherein said first and second target nucleic acids are amplified simultaneously in separate vessels.

4. The process of claim 3, wherein the reaction mixture for amplifying said first target nucleic acid comprises oligonucleotides specific for said first target nucleic acid optimized for optimal performance and the reaction mixture for amplifying said second target nucleic acid comprises said oligonucleotides specific for said second target nucleic acid optimized for optimal performance.

5. The process of claim 4, wherein the concentration of the oligonucleotides specific for said first target nucleic acid in the reaction mixture for amplifying said first target nucleic acid is substantially the same as the concentration of the oligonucleotides specific for said second target nucleic acid in the reaction mixture for amplifying said second target nucleic acid.

6. The process of claim 2, wherein said conditions suitable for transcription of RNA and said conditions sufficient for an amplification reaction are identical for the at least first and second target nucleic acids comprised in said first and second reaction vessel.

7. The process of claim 6 wherein said first and second target nucleic acids are amplified simultaneously in separate vessels.

8. The process of claim 7, wherein the reaction mixture for amplifying said first target nucleic acid comprises said an oligonucleotides specific for said first target nucleic acid optimized for optimal performance and the reaction mixture for amplifying said second target nucleic acid comprises said oligonucleotides specific for said second target nucleic acid optimized for optimal performance.

9. The process of claim 8, wherein the concentration of the oligonucleotides specific for said first target nucleic acid in the reaction mixture for amplifying said first target nucleic acid is substantially the same as the concentration of the oligonucleotides specific for said second target nucleic acid in the reaction mixture for amplifying said second target nucleic acid.

* * * * *

SEQUENCE LISTING

<160> NUMBER OF SEQ ID NOS: 92

<210> SEQ ID NO 1
<211> LENGTH: 29
<212> TYPE: DNA
<213> ORGANISM: Artificial Sequence
<220> FEATURE:
<223> OTHER INFORMATION: primer/probe

<400> SEQUENCE: 1
agtgggggga catcaagcag ccatgcaaa                                29

<210> SEQ ID NO 2
<211> LENGTH: 30
<212> TYPE: DNA
<213> ORGANISM: Artificial Sequence
<220> FEATURE:
<223> OTHER INFORMATION: primer/probe

<400> SEQUENCE: 2
agtgggggga catcaagcag ccatgcaaat                               30

<210> SEQ ID NO 3
<211> LENGTH: 23
<212> TYPE: DNA
<213> ORGANISM: Artificial Sequence
<220> FEATURE:
<223> OTHER INFORMATION: primer/probe

<400> SEQUENCE: 3
gctttcagcc cagaagtaat acc                                      23

<210> SEQ ID NO 4
<211> LENGTH: 25
<212> TYPE: DNA
<213> ORGANISM: Artificial Sequence
<220> FEATURE:
<223> OTHER INFORMATION: primer/probe

```
<400> SEQUENCE: 4
ggacacatca agcagccatg caaat                                              25

<210> SEQ ID NO 5
<211> LENGTH: 20
<212> TYPE: DNA
<213> ORGANISM: Artificial Sequence
<220> FEATURE:
<223> OTHER INFORMATION: primer/probe

<400> SEQUENCE: 5
agagaaccaa ggggaagtga                                                    20

<210> SEQ ID NO 6
<211> LENGTH: 28
<212> TYPE: DNA
<213> ORGANISM: Artificial Sequence
<220> FEATURE:
<223> OTHER INFORMATION: primer/probe

<400> SEQUENCE: 6
ataatccacc tatcccagta ggagaaat                                           28

<210> SEQ ID NO 7
<211> LENGTH: 29
<212> TYPE: DNA
<213> ORGANISM: Artificial Sequence
<220> FEATURE:
<223> OTHER INFORMATION: primer/probe

<400> SEQUENCE: 7
agtgggggga caccaggcag caatgcaaa                                          29

<210> SEQ ID NO 8
<211> LENGTH: 20
<212> TYPE: DNA
<213> ORGANISM: Artificial Sequence
<220> FEATURE:
<223> OTHER INFORMATION: primer/probe

<400> SEQUENCE: 8
catagcagga actactagta                                                    20

<210> SEQ ID NO 9
<211> LENGTH: 30
<212> TYPE: DNA
<213> ORGANISM: Artificial Sequence
<220> FEATURE:
<223> OTHER INFORMATION: primer/probe

<400> SEQUENCE: 9
ggtactagta gttcctgcta tgtcacttcc                                         30

<210> SEQ ID NO 10
<211> LENGTH: 25
<212> TYPE: DNA
<213> ORGANISM: Artificial Sequence
<220> FEATURE:
<223> OTHER INFORMATION: primer/probe

<400> SEQUENCE: 10
ctatgtcact tccccttggt tctct                                              25

<210> SEQ ID NO 11
```

```
<211> LENGTH: 30
<212> TYPE: DNA
<213> ORGANISM: Artificial Sequence
<220> FEATURE:
<223> OTHER INFORMATION: primer/probe

<400> SEQUENCE: 11
ggtactagta gttcctgcta tatcacttcc                                              30

<210> SEQ ID NO 12
<211> LENGTH: 20
<212> TYPE: DNA
<213> ORGANISM: Artificial Sequence
<220> FEATURE:
<223> OTHER INFORMATION: primer/probe

<400> SEQUENCE: 12
tccttgtctt atgtccagaa                                                         20

<210> SEQ ID NO 13
<211> LENGTH: 28
<212> TYPE: DNA
<213> ORGANISM: Artificial Sequence
<220> FEATURE:
<223> OTHER INFORMATION: primer/probe

<400> SEQUENCE: 13
tttggtcctt gtcttatgtc cagaatgc                                                28

<210> SEQ ID NO 14
<211> LENGTH: 28
<212> TYPE: DNA
<213> ORGANISM: Artificial Sequence
<220> FEATURE:
<223> OTHER INFORMATION: primer/probe

<400> SEQUENCE: 14
tactagtagt tcctgctatg tcacttcc                                                28

<210> SEQ ID NO 15
<211> LENGTH: 23
<212> TYPE: DNA
<213> ORGANISM: Artificial Sequence
<220> FEATURE:
<223> OTHER INFORMATION: primer/probe

<400> SEQUENCE: 15
tgtgttatga tggtgtttaa atc                                                     23

<210> SEQ ID NO 16
<211> LENGTH: 20
<212> TYPE: DNA
<213> ORGANISM: Artificial Sequence
<220> FEATURE:
<223> OTHER INFORMATION: primer/probe

<400> SEQUENCE: 16
actctaaagg gttcctttgg                                                         20

<210> SEQ ID NO 17
<211> LENGTH: 33
<212> TYPE: DNA
<213> ORGANISM: Artificial Sequence
<220> FEATURE:
<223> OTHER INFORMATION: primer/probe

<400> SEQUENCE: 17
```
tctgcagctt cctcattgat ggtatctttt aac                                    33

<210> SEQ ID NO 18
<211> LENGTH: 29
<212> TYPE: DNA
<213> ORGANISM: Artificial Sequence
<220> FEATURE:
<223> OTHER INFORMATION: primer/probe

<400> SEQUENCE: 18
tcagcattat cagaaggagc caccccaca                                          29

<210> SEQ ID NO 19
<211> LENGTH: 32
<212> TYPE: DNA
<213> ORGANISM: Artificial Sequence
<220> FEATURE:
<223> OTHER INFORMATION: primer/probe

<400> SEQUENCE: 19
tctgcagctt cctcattgag gtatctttta ac                                     32

<210> SEQ ID NO 20
<211> LENGTH: 41
<212> TYPE: DNA
<213> ORGANISM: Artificial Sequence
<220> FEATURE:
<223> OTHER INFORMATION: primer/probe

<400> SEQUENCE: 20
atcctgggat taaataaaat agtaagaatg tatagcccta c                            41

<210> SEQ ID NO 21
<211> LENGTH: 29
<212> TYPE: DNA
<213> ORGANISM: Artificial Sequence
<220> FEATURE:
<223> OTHER INFORMATION: primer/probe

<400> SEQUENCE: 21
accatcaatg agggaagctg cagaatggg                                          29

<210> SEQ ID NO 22
<211> LENGTH: 26
<212> TYPE: DNA
<213> ORGANISM: Artificial Sequence
<220> FEATURE:
<223> OTHER INFORMATION: primer/probe

<400> SEQUENCE: 22
tgactctggt aactagagat ccctca                                             26

<210> SEQ ID NO 23
<211> LENGTH: 30
<212> TYPE: DNA
<213> ORGANISM: Artificial Sequence
<220> FEATURE:
<223> OTHER INFORMATION: primer/probe

<400> SEQUENCE: 23
tgttcaaccc tggtatctag agatccctca                                         30

<210> SEQ ID NO 24
<211> LENGTH: 20
<212> TYPE: DNA

```
<213> ORGANISM: Artificial Sequence
<220> FEATURE:
<223> OTHER INFORMATION: primer/probe

<400> SEQUENCE: 24
ggctaactag ggacccactg                                              20

<210> SEQ ID NO 25
<211> LENGTH: 18
<212> TYPE: DNA
<213> ORGANISM: Artificial Sequence
<220> FEATURE:
<223> OTHER INFORMATION: primer/probe

<400> SEQUENCE: 25
actagggaac ccactgct                                                18

<210> SEQ ID NO 26
<211> LENGTH: 26
<212> TYPE: DNA
<213> ORGANISM: Artificial Sequence
<220> FEATURE:
<223> OTHER INFORMATION: primer/probe

<400> SEQUENCE: 26
tcagcaagcc gagtcctgcg tcgaga                                       26

<210> SEQ ID NO 27
<211> LENGTH: 27
<212> TYPE: DNA
<213> ORGANISM: Artificial Sequence
<220> FEATURE:
<223> OTHER INFORMATION: primer/probe

<400> SEQUENCE: 27
ccgctaagcc gagccctttg cgtcgga                                      27

<210> SEQ ID NO 28
<211> LENGTH: 17
<212> TYPE: DNA
<213> ORGANISM: Artificial Sequence
<220> FEATURE:
<223> OTHER INFORMATION: primer/probe

<400> SEQUENCE: 28
ggtctgaggg atctcta                                                 17

<210> SEQ ID NO 29
<211> LENGTH: 24
<212> TYPE: DNA
<213> ORGANISM: Artificial Sequence
<220> FEATURE:
<223> OTHER INFORMATION: primer/probe

<400> SEQUENCE: 29
ctgctagaga ttttccacac tgac                                         24

<210> SEQ ID NO 30
<211> LENGTH: 23
<212> TYPE: DNA
<213> ORGANISM: Artificial Sequence
<220> FEATURE:
<223> OTHER INFORMATION: primer/probe

<400> SEQUENCE: 30
ggctccacgc ttgcttgctt aaa                                          23
```

<210> SEQ ID NO 31
<211> LENGTH: 18
<212> TYPE: DNA
<213> ORGANISM: Artificial Sequence
<220> FEATURE:
<223> OTHER INFORMATION: primer/probe

<400> SEQUENCE: 31
ggctccacgc ttgcttgc                                                 18

<210> SEQ ID NO 32
<211> LENGTH: 31
<212> TYPE: DNA
<213> ORGANISM: Artificial Sequence
<220> FEATURE:
<223> OTHER INFORMATION: primer/probe

<400> SEQUENCE: 32
ttcccaaagc aagaagggtc ctaacagacc a                                  31

<210> SEQ ID NO 33
<211> LENGTH: 28
<212> TYPE: DNA
<213> ORGANISM: Artificial Sequence
<220> FEATURE:
<223> OTHER INFORMATION: primer/probe

<400> SEQUENCE: 33
tctctagcag tggcgcccga acagggac                                      28

<210> SEQ ID NO 34
<211> LENGTH: 34
<212> TYPE: DNA
<213> ORGANISM: Artificial Sequence
<220> FEATURE:
<223> OTHER INFORMATION: primer/probe

<400> SEQUENCE: 34
accagagtca cacaacagac gggcacacac tact                               34

<210> SEQ ID NO 35
<211> LENGTH: 31
<212> TYPE: DNA
<213> ORGANISM: Artificial Sequence
<220> FEATURE:
<223> OTHER INFORMATION: primer/probe

<400> SEQUENCE: 35
tcctagtcgc cgcctggtca ttcggtgttc a                                  31

<210> SEQ ID NO 36
<211> LENGTH: 25
<212> TYPE: DNA
<213> ORGANISM: Artificial Sequence
<220> FEATURE:
<223> OTHER INFORMATION: primer/probe

<400> SEQUENCE: 36
catgcaactt tttcacctct gccta                                         25

<210> SEQ ID NO 37
<211> LENGTH: 27
<212> TYPE: DNA
<213> ORGANISM: Artificial Sequence
<220> FEATURE:

```
<223> OTHER INFORMATION: primer/probe

<400> SEQUENCE: 37
aactccacag tagctccaaa ttcttta                                            27

<210> SEQ ID NO 38
<211> LENGTH: 33
<212> TYPE: DNA
<213> ORGANISM: Artificial Sequence
<220> FEATURE:
<223> OTHER INFORMATION: primer/probe

<400> SEQUENCE: 38
ccaagctgtg ccttgggtgg ctttggggca tgg                                     33

<210> SEQ ID NO 39
<211> LENGTH: 23
<212> TYPE: DNA
<213> ORGANISM: Artificial Sequence
<220> FEATURE:
<223> OTHER INFORMATION: primer/probe

<400> SEQUENCE: 39
gggattcctg taacaacaag tca                                                23

<210> SEQ ID NO 40
<211> LENGTH: 24
<212> TYPE: DNA
<213> ORGANISM: Artificial Sequence
<220> FEATURE:
<223> OTHER INFORMATION: primer/probe

<400> SEQUENCE: 40
tcttccccag aacaataaga acac                                               24

<210> SEQ ID NO 41
<211> LENGTH: 26
<212> TYPE: DNA
<213> ORGANISM: Artificial Sequence
<220> FEATURE:
<223> OTHER INFORMATION: primer/probe

<400> SEQUENCE: 41
ggcttgcaga gttctatagt gctatg                                             26

<210> SEQ ID NO 42
<211> LENGTH: 25
<212> TYPE: DNA
<213> ORGANISM: Artificial Sequence
<220> FEATURE:
<223> OTHER INFORMATION: primer/probe

<400> SEQUENCE: 42
ttgatagcaa tcggctatcg actaa                                              25

<210> SEQ ID NO 43
<211> LENGTH: 28
<212> TYPE: DNA
<213> ORGANISM: Artificial Sequence
<220> FEATURE:
<223> OTHER INFORMATION: primer/probe

<400> SEQUENCE: 43
gcttcgatac tcagtcatct cggtataa                                           28
```

```
<210> SEQ ID NO 44
<211> LENGTH: 27
<212> TYPE: DNA
<213> ORGANISM: Artificial Sequence
<220> FEATURE:
<223> OTHER INFORMATION: primer/probe

<400> SEQUENCE: 44
tctctcgcca tctcctaccg cattggc                                          27

<210> SEQ ID NO 45
<211> LENGTH: 269
<212> TYPE: DNA
<213> ORGANISM: Artificial Sequence
<220> FEATURE:
<223> OTHER INFORMATION: internal control nucleic acid

<400> SEQUENCE: 45
aattcaagct tagatctagc tttgcctgct tgatagcaat cggctatcga ctaatgactg      60
tcctggcggt ctctcgccat ctcctaccgc attggctcat aggtaagctc gctgtcaccc     120
agtacggagg tgccagtaga ttattagaga cagtcgccaa tcgatcgtta taccgagatg     180
actgagtatc gaagctacat tgtagccgca cataggacca cccatcttca tgttgaaaca     240
tgaggattac ccatgtggat ccaagcttg                                       269

<210> SEQ ID NO 46
<211> LENGTH: 235
<212> TYPE: DNA
<213> ORGANISM: Artificial Sequence
<220> FEATURE:
<223> OTHER INFORMATION: internal control nucleic acid

<400> SEQUENCE: 46
gggctgcagg tcgactctag attctaagaa tttgatgggc ttttctact aattactatt       60 agtatattgc catctttaac acttagaccg aagtgtgctg aagttccagt ggccggccca     120
gacctgggaa gttgcaagga cttaaacgaa tgcaagcgat catatcttga aaaattataa    180
ccagaggatc gatgaaaaaa atttcttaga gctttggatc cccgggcgag ctccc          235

<210> SEQ ID NO 47
<211> LENGTH: 350
<212> TYPE: DNA
<213> ORGANISM: Artificial Sequence
<220> FEATURE:
<223> OTHER INFORMATION: internal control nucleic acid

<400> SEQUENCE: 47
cgactctaga tgaagggagc cttagaacgg ggctgcgcta gctggcatca aagtccgtca      60
gagctcaacc ctccaacgag gattcctgaa tactcgaaag tcagtgtgca gttactaaca    120
acagctgctc gacctcgggg tctcgaacaa tccatacctg ctatcgctgc cttcagacat    180
acggatgggc taggaggcaa gagctacctg tctcaacgaa ctatcggagt gggacccgat    240
gaagctgtca gcgccacttc cggcggtaag gctttaaaac gcgcccgccg gttatcacgc    300
gcggggagca cagcgcggac tgacgtgctg ggaagcaccg gttaaggatc                350

<210> SEQ ID NO 48
<211> LENGTH: 470
<212> TYPE: DNA
<213> ORGANISM: Artificial Sequence
<220> FEATURE:
<223> OTHER INFORMATION: internal control nucleic acid
```

<400> SEQUENCE: 48

```
cgactctaga aactgggtag taactgcggg ggcgaatgat gcaggcttca gaaattaaac    60
tcaatagtat ccggtgtctc aatcttttc gggccaggcg gcggtggacg acagacaatt   120
ttacgatttt ggttccggtc acaaccgcgc catacatgtc aagaatgaag tgggcgaacg   180
ctagaaaact gacgccagca attaagtgag tcggggcgtg gtgactccca cgtaaaaagc   240
ccctaccccg caccgttacg aagtatcaaa acgggacgcg cacgaaccga cgattggtac   300
tgtataagcg gcccgacgaa ctcaaaatcc caagtgaatc tatgaaatct acatcgcgtt   360
tataatctac ggggtgtaaa cggatgagaa ttggccaaac ggaggcacac acgcgtgcaa   420
tgcgccgacc ctgagaaaag tatcatgtgc gtcggccaca ggatccccgg             470
```

<210> SEQ ID NO 49
<211> LENGTH: 22
<212> TYPE: DNA
<213> ORGANISM: Artificial Sequence
<220> FEATURE:
<223> OTHER INFORMATION: primer / probe

<400> SEQUENCE: 49

```
ccaagcttca ccatagatca ct                                             22
```

<210> SEQ ID NO 50
<211> LENGTH: 24
<212> TYPE: DNA
<213> ORGANISM: Artificial Sequence
<220> FEATURE:
<223> OTHER INFORMATION: primer / probe

<400> SEQUENCE: 50

```
ggcgacactc caccatagat cact                                           24
```

<210> SEQ ID NO 51
<211> LENGTH: 31
<212> TYPE: DNA
<213> ORGANISM: Artificial Sequence
<220> FEATURE:
<223> OTHER INFORMATION: primer / probe

<400> SEQUENCE: 51

```
ccaagcttag atcactcccc tgtgaggaac t                                   31
```

<210> SEQ ID NO 52
<211> LENGTH: 30
<212> TYPE: DNA
<213> ORGANISM: Artificial Sequence
<220> FEATURE:
<223> OTHER INFORMATION: primer / probe

<400> SEQUENCE: 52

```
ccaagcttca cgcagaaagc gtctagccat                                     30
```

<210> SEQ ID NO 53
<211> LENGTH: 24
<212> TYPE: DNA
<213> ORGANISM: Artificial Sequence
<220> FEATURE:
<223> OTHER INFORMATION: primer / probe

<400> SEQUENCE: 53

```
gcagaaagcg tctagccatg gcgt                                           24
```

<210> SEQ ID NO 54
<211> LENGTH: 26
<212> TYPE: DNA
<213> ORGANISM: Artificial Sequence
<220> FEATURE:
<223> OTHER INFORMATION: primer / probe

<400> SEQUENCE: 54
acgcagaaag cgtctagcca tggcgt                                          26

<210> SEQ ID NO 55
<211> LENGTH: 30
<212> TYPE: DNA
<213> ORGANISM: Artificial Sequence
<220> FEATURE:
<223> OTHER INFORMATION: primer / probe

<400> SEQUENCE: 55
cctccaggac cccccctccc gggagagcca                                      30

<210> SEQ ID NO 56
<211> LENGTH: 27
<212> TYPE: DNA
<213> ORGANISM: Artificial Sequence
<220> FEATURE:
<223> OTHER INFORMATION: primer / probe

<400> SEQUENCE: 56
gagtacaccg gaattgccag gacgacc                                         27

<210> SEQ ID NO 57
<211> LENGTH: 21
<212> TYPE: DNA
<213> ORGANISM: Artificial Sequence
<220> FEATURE:
<223> OTHER INFORMATION: primer / probe

<400> SEQUENCE: 57
acccgctcaa tgcctggaga t                                               21

<210> SEQ ID NO 58
<211> LENGTH: 22
<212> TYPE: DNA
<213> ORGANISM: Artificial Sequence
<220> FEATURE:
<223> OTHER INFORMATION: primer / probe

<400> SEQUENCE: 58
cgaagcttgc tagccgagta gt                                              22

<210> SEQ ID NO 59
<211> LENGTH: 24
<212> TYPE: DNA
<213> ORGANISM: Artificial Sequence
<220> FEATURE:
<223> OTHER INFORMATION: primer / probe

<400> SEQUENCE: 59
ccgcaagact gctagccgag tagt                                            24

<210> SEQ ID NO 60
<211> LENGTH: 25
<212> TYPE: DNA
<213> ORGANISM: Artificial Sequence
<220> FEATURE:
<223> OTHER INFORMATION: primer / probe

```
<400> SEQUENCE: 60
gttgggtcgc gaaaggcctt gtggt                                        25

<210> SEQ ID NO 61
<211> LENGTH: 30
<212> TYPE: DNA
<213> ORGANISM: Artificial Sequence
<220> FEATURE:
<223> OTHER INFORMATION: primer / probe

<400> SEQUENCE: 61
ggtgcttgcg agtgccccgg gaggtctcgt                                   30

<210> SEQ ID NO 62
<211> LENGTH: 24
<212> TYPE: DNA
<213> ORGANISM: Artificial Sequence
<220> FEATURE:
<223> OTHER INFORMATION: primer / probe

<400> SEQUENCE: 62
gacttccgag cggtcgcaac ctcg                                         24

<210> SEQ ID NO 63
<211> LENGTH: 26
<212> TYPE: DNA
<213> ORGANISM: Artificial Sequence
<220> FEATURE:
<223> OTHER INFORMATION: primer / probe

<400> SEQUENCE: 63
gcagaaagcg tctagccatg gcgtta                                       26

<210> SEQ ID NO 64
<211> LENGTH: 25
<212> TYPE: DNA
<213> ORGANISM: Artificial Sequence
<220> FEATURE:
<223> OTHER INFORMATION: primer / probe

<400> SEQUENCE: 64
gcaagcaccc tataggcagt accac                                        25

<210> SEQ ID NO 65
<211> LENGTH: 33
<212> TYPE: DNA
<213> ORGANISM: Artificial Sequence
<220> FEATURE:
<223> OTHER INFORMATION: primer / probe

<400> SEQUENCE: 65
gggagagcca tagtggtctg cggaaccggt gag                               33

<210> SEQ ID NO 66
<211> LENGTH: 25
<212> TYPE: DNA
<213> ORGANISM: Artificial Sequence
<220> FEATURE:
<223> OTHER INFORMATION: primer / probe

<400> SEQUENCE: 66
cccaacacta ctcggctagc agtct                                        25

<210> SEQ ID NO 67
<211> LENGTH: 26
```

```
<212> TYPE: DNA
<213> ORGANISM: Artificial Sequence
<220> FEATURE:
<223> OTHER INFORMATION: primer / probe

<400> SEQUENCE: 67
aaggcctttc gcgacccaac actact                                            26

<210> SEQ ID NO 68
<211> LENGTH: 26
<212> TYPE: DNA
<213> ORGANISM: Artificial Sequence
<220> FEATURE:
<223> OTHER INFORMATION: primer / probe

<400> SEQUENCE: 68
cacaaggcct ttcgcgaccc aacact                                            26

<210> SEQ ID NO 69
<211> LENGTH: 24
<212> TYPE: DNA
<213> ORGANISM: Artificial Sequence
<220> FEATURE:
<223> OTHER INFORMATION: primer / probe

<400> SEQUENCE: 69
ctcgcaagca ccctatcagg cagt                                              24

<210> SEQ ID NO 70
<211> LENGTH: 33
<212> TYPE: DNA
<213> ORGANISM: Artificial Sequence
<220> FEATURE:
<223> OTHER INFORMATION: primer / probe

<400> SEQUENCE: 70
ccgggagagc catagtggtc tgcggaaccg gtg                                    33

<210> SEQ ID NO 71
<211> LENGTH: 33
<212> TYPE: DNA
<213> ORGANISM: Artificial Sequence
<220> FEATURE:
<223> OTHER INFORMATION: primer / probe

<400> SEQUENCE: 71
caccggttcc gcagaccact atggctctcc cgg                                    33

<210> SEQ ID NO 72
<211> LENGTH: 26
<212> TYPE: DNA
<213> ORGANISM: Artificial Sequence
<220> FEATURE:
<223> OTHER INFORMATION: primer / probe

<400> SEQUENCE: 72
cactcgcaag caccctatca ggcagt                                            26

<210> SEQ ID NO 73
<211> LENGTH: 29
<212> TYPE: DNA
<213> ORGANISM: Artificial Sequence
<220> FEATURE:
<223> OTHER INFORMATION: primer / probe

<400> SEQUENCE: 73
```
gggaattcgc aagcacccta tcaggcagt                                    29

<210> SEQ ID NO 74
<211> LENGTH: 23
<212> TYPE: DNA
<213> ORGANISM: Artificial Sequence
<220> FEATURE:
<223> OTHER INFORMATION: primer / probe

<400> SEQUENCE: 74
cgaggttgcg accgctcgga agt                                          23

<210> SEQ ID NO 75
<211> LENGTH: 21
<212> TYPE: DNA
<213> ORGANISM: Artificial Sequence
<220> FEATURE:
<223> OTHER INFORMATION: primer / probe

<400> SEQUENCE: 75
aggttgcgac cgctcggaag t                                            21

<210> SEQ ID NO 76
<211> LENGTH: 33
<212> TYPE: DNA
<213> ORGANISM: Artificial Sequence
<220> FEATURE:
<223> OTHER INFORMATION: primer / probe

<400> SEQUENCE: 76
caccggttcc gcagaccact atggctctcc cgg                               33

<210> SEQ ID NO 77
<211> LENGTH: 21
<212> TYPE: DNA
<213> ORGANISM: Artificial Sequence
<220> FEATURE:
<223> OTHER INFORMATION: primer / probe

<400> SEQUENCE: 77
aatgccatag aggggccaag g                                            21

<210> SEQ ID NO 78
<211> LENGTH: 21
<212> TYPE: DNA
<213> ORGANISM: Artificial Sequence
<220> FEATURE:
<223> OTHER INFORMATION: primer / probe

<400> SEQUENCE: 78
attgccatag aggggccaag g                                            21

<210> SEQ ID NO 79
<211> LENGTH: 31
<212> TYPE: DNA
<213> ORGANISM: Artificial Sequence
<220> FEATURE:
<223> OTHER INFORMATION: primer / probe

<400> SEQUENCE: 79
cagaattcat tgccatagag gggccaagga t                                 31

<210> SEQ ID NO 80
<211> LENGTH: 22
<212> TYPE: DNA
<213> ORGANISM: Artificial Sequence

```
<220> FEATURE:
<223> OTHER INFORMATION: primer / probe

<400> SEQUENCE: 80
cagaattcgc cctcattgcc at                                          22

<210> SEQ ID NO 81
<211> LENGTH: 24
<212> TYPE: DNA
<213> ORGANISM: Artificial Sequence
<220> FEATURE:
<223> OTHER INFORMATION: primer / probe

<400> SEQUENCE: 81
ctcgcaagca ccctatcagg caga                                        24

<210> SEQ ID NO 82
<211> LENGTH: 24
<212> TYPE: DNA
<213> ORGANISM: Artificial Sequence
<220> FEATURE:
<223> OTHER INFORMATION: primer / probe

<400> SEQUENCE: 82
cccaccccaa gccctcattg ccat                                        24

<210> SEQ ID NO 83
<211> LENGTH: 24
<212> TYPE: DNA
<213> ORGANISM: Artificial Sequence
<220> FEATURE:
<223> OTHER INFORMATION: primer / probe

<400> SEQUENCE: 83
ttgccggaaa gactgggtcc tttc                                        24

<210> SEQ ID NO 84
<211> LENGTH: 24
<212> TYPE: DNA
<213> ORGANISM: Artificial Sequence
<220> FEATURE:
<223> OTHER INFORMATION: primer / probe

<400> SEQUENCE: 84
caaaagaaac acaaaccgcc gccc                                        24

<210> SEQ ID NO 85
<211> LENGTH: 24
<212> TYPE: DNA
<213> ORGANISM: Artificial Sequence
<220> FEATURE:
<223> OTHER INFORMATION: primer / probe

<400> SEQUENCE: 85
ccagcccatc ccgaaagatc ggcg                                        24

<210> SEQ ID NO 86
<211> LENGTH: 18
<212> TYPE: DNA
<213> ORGANISM: Artificial Sequence
<220> FEATURE:
<223> OTHER INFORMATION: primer / probe

<400> SEQUENCE: 86
tgtccggtca tttgggcg                                               18
```

```
<210> SEQ ID NO 87
<211> LENGTH: 21
<212> TYPE: DNA
<213> ORGANISM: Artificial Sequence
<220> FEATURE:
<223> OTHER INFORMATION: primer / probe

<400> SEQUENCE: 87
aaacccactc tatgtccggt c                                              21

<210> SEQ ID NO 88
<211> LENGTH: 21
<212> TYPE: DNA
<213> ORGANISM: Artificial Sequence
<220> FEATURE:
<223> OTHER INFORMATION: primer / probe

<400> SEQUENCE: 88
gtacgccgga attgccggaa a                                              21

<210> SEQ ID NO 89
<211> LENGTH: 21
<212> TYPE: DNA
<213> ORGANISM: Artificial Sequence
<220> FEATURE:
<223> OTHER INFORMATION: primer / probe

<400> SEQUENCE: 89
cctcaaagaa aaaccaaaag a                                              21

<210> SEQ ID NO 90
<211> LENGTH: 21
<212> TYPE: DNA
<213> ORGANISM: Artificial Sequence
<220> FEATURE:
<223> OTHER INFORMATION: primer / probe

<400> SEQUENCE: 90
tggcgtctcc cacgcggctg g                                              21

<210> SEQ ID NO 91
<211> LENGTH: 21
<212> TYPE: DNA
<213> ORGANISM: Artificial Sequence
<220> FEATURE:
<223> OTHER INFORMATION: primer / probe

<400> SEQUENCE: 91
ctttccccag gacctgccgg t                                              21

<210> SEQ ID NO 92
<211> LENGTH: 26
<212> TYPE: DNA
<213> ORGANISM: Artificial Sequence
<220> FEATURE:
<223> OTHER INFORMATION: primer / probe

<400> SEQUENCE: 92
catagtggtc tgcggaaccg gtgagt                                         26
```